United States Patent
Whitlon et al.

(10) Patent No.: US 9,150,533 B2
(45) Date of Patent: Oct. 6, 2015

(54) LOCAL COCHLEAR APPLICATION OF STATINS FOR STIMULATING NEURITE REGROWTH IN THE COCHLEA

(71) Applicants: Donna S. Whitlon, Deerfield, IL (US); Claus-Peter Richter, Skokie, IL (US)

(72) Inventors: Donna S. Whitlon, Deerfield, IL (US); Claus-Peter Richter, Skokie, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/105,582

(22) Filed: Dec. 13, 2013

(65) Prior Publication Data

US 2014/0179723 A1    Jun. 26, 2014

Related U.S. Application Data

(60) Provisional application No. 61/745,292, filed on Dec. 21, 2012.

(51) Int. Cl.

| | |
|---|---|
| *C07D 309/30* | (2006.01) |
| *C07C 69/28* | (2006.01) |
| *C07D 307/34* | (2006.01) |
| *C07D 209/24* | (2006.01) |
| *C07D 213/55* | (2006.01) |
| *C07D 207/34* | (2006.01) |
| *A61K 31/366* | (2006.01) |
| *A61K 31/40* | (2006.01) |
| *A61K 31/405* | (2006.01) |
| *A61K 31/4418* | (2006.01) |

(52) U.S. Cl.
CPC ............ *C07D 309/30* (2013.01); *A61K 31/366* (2013.01); *A61K 31/40* (2013.01); *A61K 31/405* (2013.01); *A61K 31/4418* (2013.01); *C07D 207/34* (2013.01); *C07D 209/24* (2013.01); *C07D 213/55* (2013.01)

(58) Field of Classification Search
None
See application file for complete search history.

(56) References Cited

PUBLICATIONS

Shimamura et al., 38(12) Stroke 3251-3258 (2007).*
Cai et al., 71(5) ORL 244-250 (2009).*
Brand et al., 12(114) BMC Neuroscience 1-10 (2011).*
Humes L, Joellenbeck L, Durch J (Eds.) "Noise and Military Service: Implications for Hearing Loss and Tinnitus" (National Academies Press, (Washington, D.C. (USA)) (2006).
Yankaskas K, "Prelude: noise-induced tinnitus and hearing loss in the military," Hearing Research 295:3-8 (2013).
Kujawa SG and Liberman MC "Adding insult to injury: Cochlear nerve degeneration after "Temporary" noise-induced hearing loss" Journal of Neuroscience 29:14077-14085 (2009).
Lie M, Grover M, Whitlon DS "Accelerated neurite growth from spiral ganglion neurons exposed to the Rho kinas inhibitor H1157" Neuroscience 169:855-862 (2010).
Taylor MM, Creelman CD. "Pest: Efficient estimates on probability functions" J Acoust Soc Am.41:782-787 (1967).
Gummer AW, Smolders JWT, Klinke R. "Basilar membrane motion in the pigeon measured with the Mössbauer technique" Hear Res. 29:63-92 (1987).
Whitlon, DS et al., "Survival and morphology of auditory neurons in dissociated cultures of newborn mouse spiral ganglion," Neuroscience, 138:653-662 (2006).
Richter CP et al., "Optical stimulation of auditory neurons: Effects of acute and chronic deafening" Hear. Res. 242:42-51 (2008).
White DL et al. "The chemical nature of osmium tetroxide fixation and staining of membranes by x-ray photoelectron spectroscopy" Biochim Biophys Acta 436:577-92 (1976).

\* cited by examiner

*Primary Examiner* — Timothy R Rozof
(74) *Attorney, Agent, or Firm* — Klintworth & Rozenblat IP LLC

(57) ABSTRACT

Statin compositions are disclosed for stimulating neurite growth from spiral ganglion neurons in the inner ear and methods for preventing damage to or treating damage of auditory neurons and/or hair cells of the cochlea following acoustic or toxic insult.

5 Claims, 23 Drawing Sheets

LOCAL COCHLEAR APPLICATION OF STATINS FOR STIMULATING NEURITE REGROWTH IN THE COCHLEA

CROSS-REFERENCE TO RELATED APPLICATIONS

This application claims benefit of priority under 35 U.S.C. 119 to U.S. provisional patent application Ser. No. 61/745,292 filed Dec. 21, 2012, and entitled "LOCAL COCHLEAR APPLICATION FOR STIMULATING NEURITE REGROWTH IN THE COCHLEA," the contents of which are herein incorporated by reference in its entirety.

STATEMENT REGARDING FEDERALLY SPONSORED RESEARCH OR DEVELOPMENT

This invention was made with government support under N00014-12-1-0173 awarded by the Office of Naval Research. The government has certain rights in the invention.

BACKGROUND

1. Technical Field

The present disclosure relates to compositions and methods for stimulating auditory neuron growth to prevent or treat hearing loss. In particular, statin compositions are disclosed for stimulating neurite growth from spiral ganglion neurons in the inner ear and methods for preventing damage to or treating damage of auditory neurons and/or hair cells of the cochlea following acoustic or ototoxic insult.

2. Description of Related Art

Continuous exposure to high decibel level acoustic insults or exposure to certain antibiotics or chemical toxins can result in severe inner ear damage, promote hearing impairment and deafness, and ultimately interfere with job performance (for example, Humes L, Joellenbeck L, Durch J (2005) Noise and Military Service Implications for Hearing Loss and Tinnitus: National Academies Press; Yankaskas K (2013) Prelude: noise-induced tinnitus and hearing loss in the military. Hearing Research 295: 3-8.). Recent evidence indicates that there are auditory insults, whose effects were previously unrecognized with standard audiograms, that can initiate an irreversible decay in hearing acuity, but do not cause obvious physical damage to the sound transducing cells (hair cells) in the cochlea. In fact, when one considers these formerly invisible sources of cochlear damage, it is easier to put in perspective the huge financial outlay (over $1 billion per year in FY2013) the U.S. Veterans Administration finds necessary to care for service-related hearing disabilities.

Permanent Threshold Shift (PTS) and Temporary Threshold Shift (TTS)

In the clinical assessment of hearing, "threshold" refers to the lowest sound level that a subject can hear. Physical harm to the ear—such as those induced by blasts, explosions shock waves and unremitting high decibel noise—causes a permanent elevation in the threshold needed to detect sound (permanent threshold shift, PTS). On the other hand, intense loud sounds of short duration, such as those produced by a period of weapons fire on a range or in combat, or at a music concert, or in close proximity to fireworks or using loud headphones can cause a "temporary" deafness as measured by reversible elevation in the threshold. Because, over time, the elevated threshold returns to normal, the episode is called "temporary threshold shift" or TTS. Until recently, TTS was thought to reflect a transitory damage to hearing, and the return of the threshold to its pre-noise exposure level, was taken as evidence that the subject was "cured". Recent studies in guinea pigs and mice indicate that this previously misunderstood "temporary" hearing injury is not "temporary" and that results from threshold shift analysis alone fail to reveal serious aspects of hearing damage. In particular neurons that are required to encode acoustic information at higher sound levels are damaged. Therefore, speech recognition in noisy listening environments becomes difficult.

The cochlea is the peripheral organ of hearing (FIG. 1). It lies between the middle ear and the brain. The neurons of the spiral ganglion are situated within the cochlea in a boney pocket close to the axis of the spiral (FIG. 1, blue circle). Spiral ganglion neurons are bipolar, meaning they have two nerve fibers arising from their cell bodies. Hair cells, located at the edge of the cochlear spiral (FIG. 1, green circle; FIG. 2), detect and transduce auditory information. The peripherally oriented nerve fibers (FIG. 3, path A) of the spiral ganglion neurons synapse on hair cells. The centrally oriented nerve fibers (FIG. 3, path B) collect within the cochlea to form the cochlear part of the auditory (VIIth nerve). These fibers grow to the brain and eventually separate to synapse on nerve cells in the cochlear nucleus.

Auditory information from the periphery is first carried to the brain through this nerve fiber network. Consequently, anything that interferes with the transfer of information (for example, loss of hair cells, loss of neurons, loss of synapses, loss of nerve fibers) will cause hearing loss.

One of the defining elements of auditory information is that of the frequency of sound. The ability to encode frequency information and transmit it to the brain underlies the human ability to interpret pitch and speech. A gradient of sound frequencies is encoded along the spiral of the cochlea, from base to apex. This frequency/place representation of sound (called "tonotopic") is carried through the spiral ganglion to the brain stem and is preserved up to the auditory cortex (FIG. 4). The more discrete frequencies that can be represented in the ear and carried to the cortex, the better the sound interpretation will be by the listener.

Pathology of Permanent (PTS) and Temporary (TTS) Threshold Shift

PTS is primarily sensorineural in origin and is due to loss of function or degeneration of hair cells or spiral ganglion neurons, neither of which will spontaneously regenerate after damage. After hair cells degenerate in PTS, neurons respond in at least two ways. Some immediately die. In others, the disconnected peripheral fiber (FIG. 3, path A) retracts (degenerates). But the centrally-connected fibers (FIG. 3, path B) degenerate more slowly. This means that even after the loss of the peripheral nerve fiber or synaptic input, the neuron can remain connected to the brain stem in a more or less tonotopic organization.

The only treatments currently available for PTS are hearing aid devices (which depend on preservation of at least some of the neurons and hair cells) or cochlear implant (CI) devices. A CI device consists of a speech processor and an array of electrodes which is inserted into scala tympani of the cochlea. Electrical current is delivered through the electrodes to the tissue to stimulate the remaining spiral ganglion cells. CI device electrodes are aligned along the tonotopically-organized spiral ganglion to model the tonotopic stimulation of the cochlea by acoustical stimuli in a pristine cochlea. Current spreads in the tissue and stimulation at neighboring electrode contacts results in confusing information because the current fields overlap. The further the target neurons are located from the electrode contacts the more current is required for stimulation, which worsens the overlap of the current fields. Hence, current spread in the tissue limits the number of electrodes that can encode discrete frequency information. Various authors have suggested the desirability of intervening to maintain spiral ganglion neuronal survival and/or to stimulate the regrowth of their peripheral neurites.

TTS Differ Significantly from PTS

For TTS, the hair cells do not degenerate after the insult to the ear. Despite the overall preservation of hair cells, a population of synapses between the inner hair cell and spiral ganglion peripheral fibers degenerate irreversibly almost immediately after sound exposure. Fibers synapsing on inner hair cells can be categorized as those that respond to low level sounds and others that respond to high level sound. The fibers that respond to low level tones saturate in their response at sound levels 20-40 dB above their threshold, while some of neurons with high threshold increase their activity over a larger range of sound intensities. Thus, the second type of fiber improves hearing in noisy environments where the neurons that respond to low sound levels are already saturated. In noise-induced TTS, the neurons and synapses that response to high level sound will be damaged. In other words, thresholds to pure tones do not change. The effect of TTS damage is on the ability to encode large ranges of sound levels and the ability to encode sound at higher levels. But the effect is not only on the synapses. TTS insult initiates the inexorable, but previously unknown, degeneration of spiral ganglion neurons over time. The long-term fate of spiral ganglion cells is thought to be sealed within the first 24 hours post exposure (Kujawa S G and Libemnan M C (2009) Adding insult to injury: Cochlear nerve degeneration after "Temporary" noise-induced hearing loss. Journal of Neuroscience 29:14077-14085.)

Compounds

A number of compounds have been investigated by others for their ability to effect or maintain neuron growth. These compound studies are summarized below.

(a) Neurotrophins

A variety of reports have shown that two neurotrophins, brain derived neurotrophic factor (BDNF) and neurotrophic factor 3 (NT3) will maintain neuronal survival in vivo as long as they are continuously applied to the cochlea. To provide a continuous supply of growth factors, various studies have attempted to biologically generate NT3 or BDNF with the use of genetically engineered viruses or genetically modified "cell factories". Success has been limited and has been dependent on the time after deafness that treatment is initiated, the cell types that undergo transduction, the concentrations of neurotrophins that the cell factories can generate in the ear, and the length of time that they are producing sufficient amounts of the neurotrophins. A few studies in vivo have suggested that neurotrophins can also stimulate neurite growth, but this stimulation does not seem to be robust and the design of the experiments have not clearly differentiated effects on neuronal survival, neurite repair, neurite source (local or from the brain) and neurite branching. Neurotrophin studies have provided valuable information on spiral ganglion cell survival and given insight into mechanisms for nearly 20 years, but they have not led to drugs for use in the ear.

(b) Antioxidants

The effects of antioxidant related compounds on the cochlea and on hearing after noise exposure have been reported. Hair cells can be partly protected from the initial effects of noise, if certain antioxidant(s) are provided before, during and after the noise insult. There is also some data that suggests that certain antioxidants may have some protective effect on neurons, although there is no information on the specific effects of antioxidants on neurite growth.

(c) Other Compound

Several other biological factors have been tested for effects on hearing, hair cells and or neurons. These include GDNF, βFGF, erythropoietin, lithium, Bone morphogenetic protein (BMP) 2; (BMP4), depolarization, cpt-cAMP, leukemia inhibitory factor. These factors may shed light on biochemical pathways important to survival and neurite growth of spiral ganglion neurons. Lie M, Grover M, Whitlon D S (2010) Accelerated neurite growth from spiral ganglion neurons exposed to the Rho kinas inhibitor H1152. Neuroscience 169: 855-862 demonstrated that the Rho kinase inhibitor H1152 can stimulate neurite growth from spiral ganglion neurons in vitro, being the first demonstration that inhibiting the activity of an enzyme would increase neurite length from spiral ganglion neurons.

Past PTS studies demonstrated that the central fibers of spiral ganglion neurons degenerate more slowly than peripheral fibers. Thus, the tonotopic orientation can be more or less maintained in the brain even after the peripheral synapses (and thus transfer of information from the hair cells to the neurons) are lost. Yet no compounds exist for maintaining spiral ganglion neurons and stimulating the regeneration of their nerve fibers and synapses. Consequently, no known compositions are available that are suitable for preventing or treating auditory neuron damage of the cochlea and acquired deafness. There is a need for such compositions and methods.

SUMMARY

In a first respect, a pharmaceutical composition for preventing or treating hearing loss in a subject is provided. The pharmaceutical composition includes a statin or a pharmaceutically acceptable salt thereof.

In a second respect, a method of stimulating neurite growth from spiral ganglion neurons in the inner ear is provided. The method includes the step of contacting a neurite with a statin, or a pharmaceutically acceptable salt thereof.

In a third respect, a method of preventing or treating hearing loss in a subject is provided. The method includes the step of administering to the subject a statin or a pharmaceutically acceptable salt thereof.

DETAILED DESCRIPTION

Figure 1:
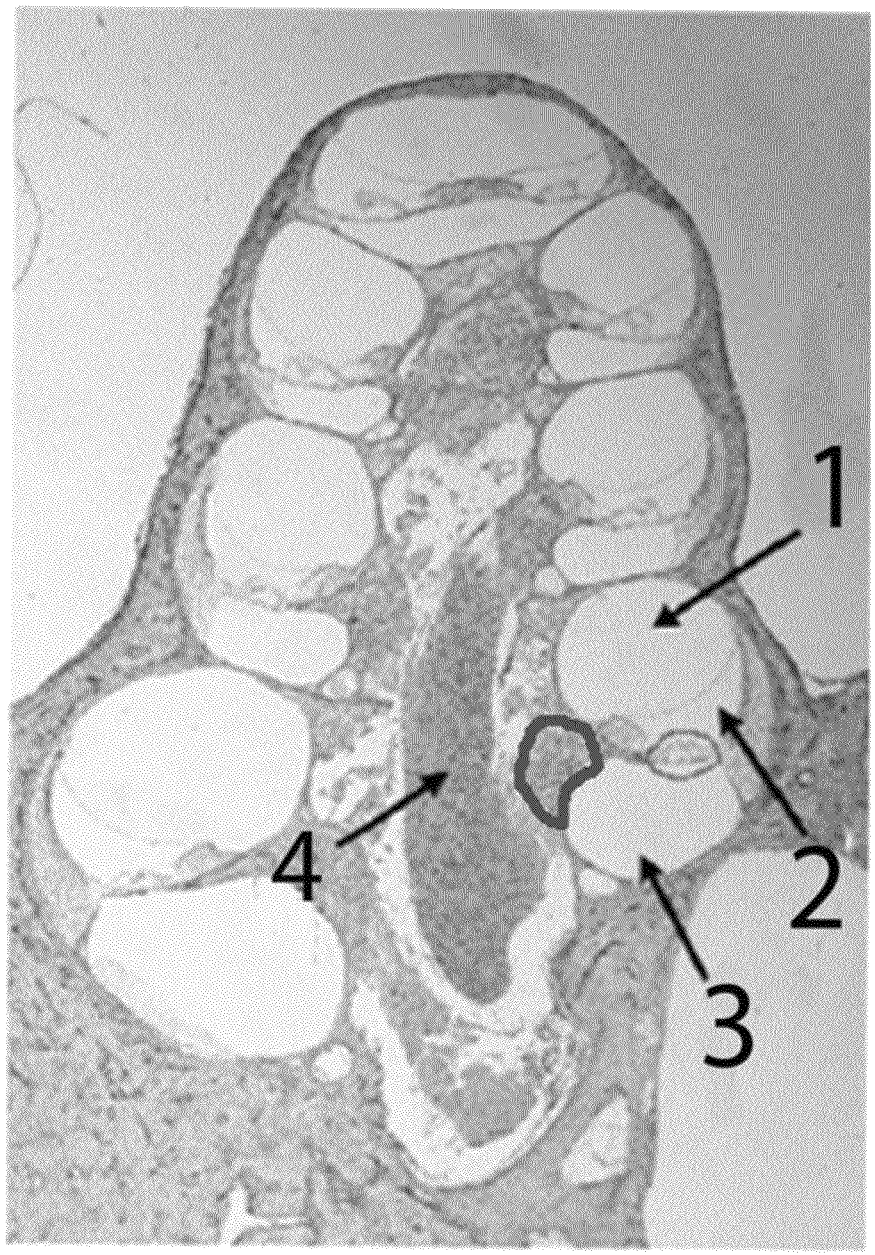
FIG. 1 depicts a mid-modiolar cut through the cochlea, wherein a cross-section of one turn of the spiral ganglion (blue circle) and the region of hair cells (green oval) are indicated. 1-scala vestibule; 2-scala media; 3-scala tympani; 4-modiolus leading to the auditory nerve.
Figure 2:
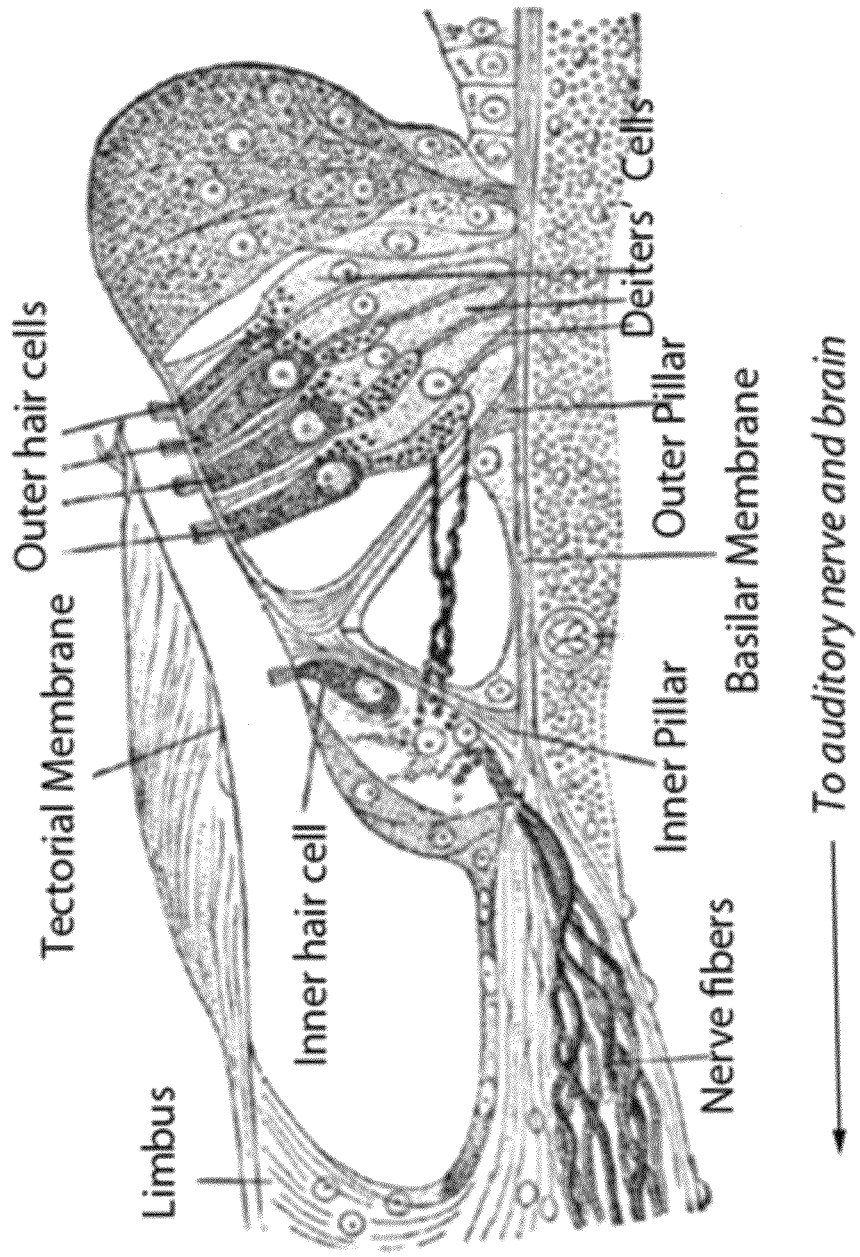
FIG. 2 depicts a cross section through the region of the organ of Corti, indicating the inner and outer hair cells that lie at the edge of the cochlear spiral, and the incoming nerve fibers.
Figure 3:
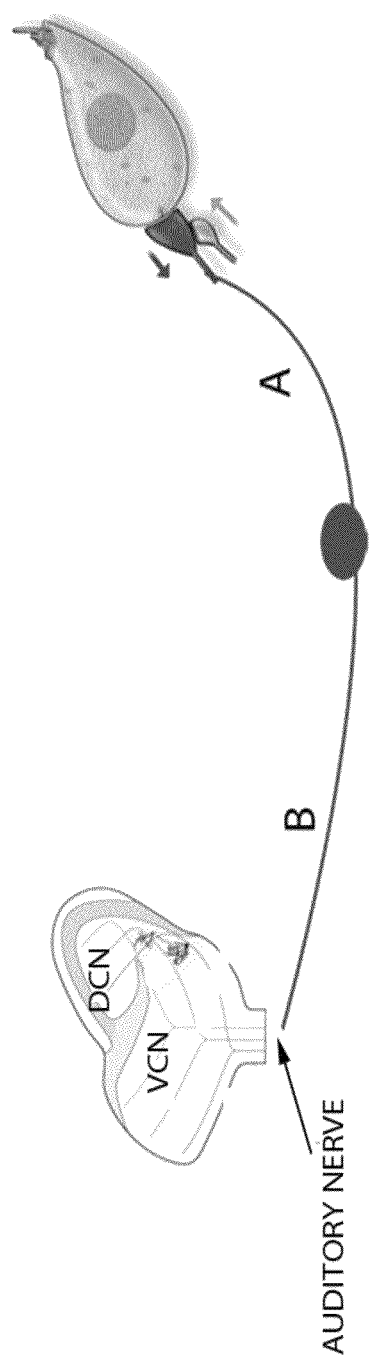
FIG. 3 depicts the route of peripherally-oriented and centrally-oriented nerve fibers from spiral ganglion neurons. Path A indicates that peripherally-oriented nerve fibers of the spiral ganglion neurons synapse on hair cells; path B indicates that centrally oriented nerve fibers that collect within the cochlea to form the cochlear part of the auditory (VIIIth) nerve, synapse on neurons in the cochlear nucleus of the brain.
Figure 4:
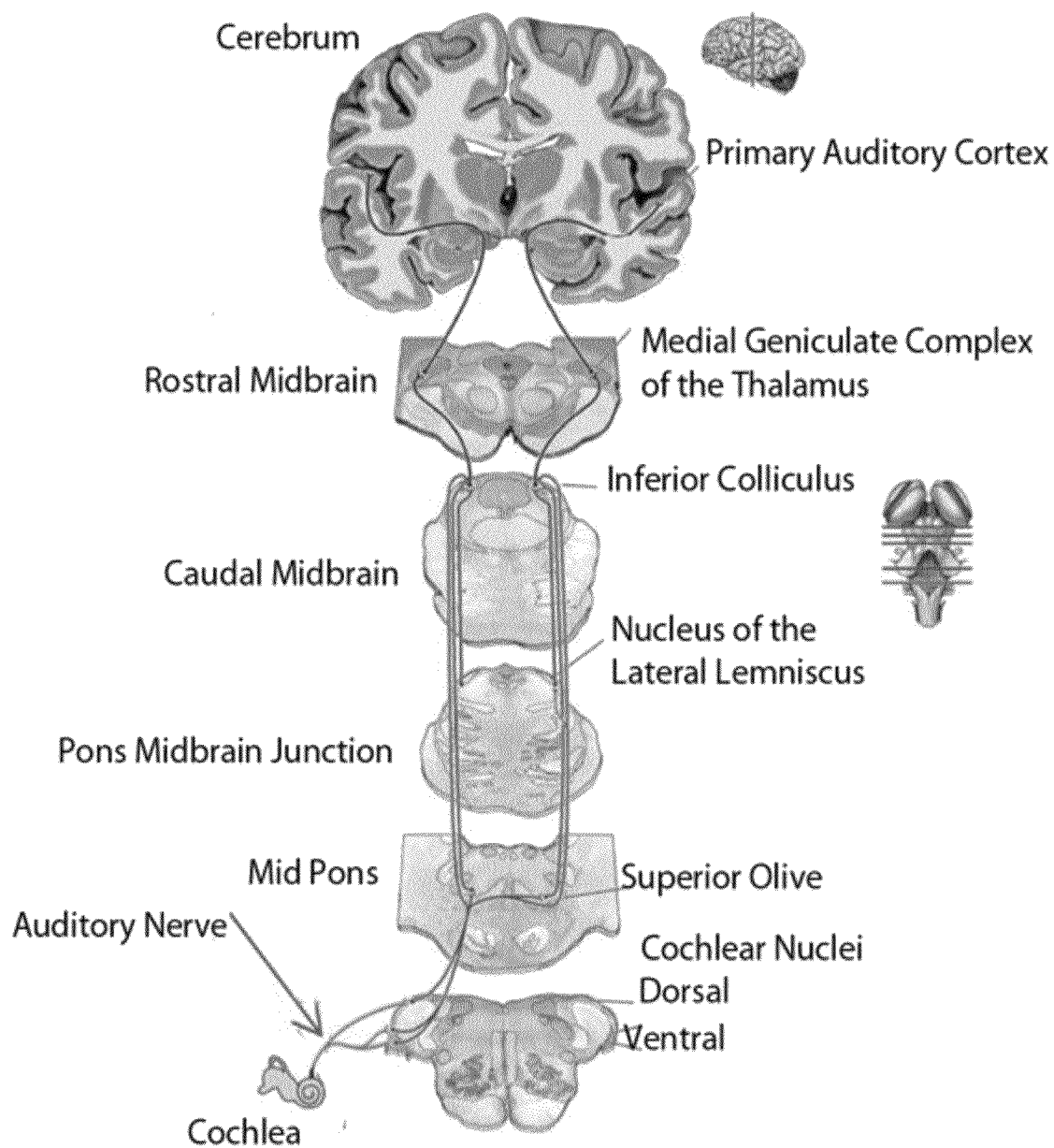
FIG. 4 depicts the neural connection of the spiral ganglion neurons of the cochlea to the cochlear nucleus and the paths through the brain to the primary auditory cortex.

A robust, in vitro, phenotypic screen for spiral ganglion neurons is disclosed that led to the discovery of compounds having neurite promoting activities. Lead compounds identified by the screen have protective effects on hearing from acute acoustic injury when administered in a guinea pig model of PTS. The compounds, pharmaceutical compositions and methods for stimulating neurite growth from spiral ganglion neurons of the cochlea to prevent or treat hearing loss following acoustic insult to the cochlea are presented herein.

DEFINITIONS

To aid in understanding the invention, several terms are defined below.

Terms used herein am intended as "open" terms (for example, the term "including" should be interpreted as "including but not limited to," the term "having" should be interpreted as "having at least," the term "includes" should be interpreted as "includes but is not limited to," etc.).

The articles "a" and "an" refer to one or to more than one (for example, to at least one) of the grammatical object of the article.

The terms "about" and "approximately" shall generally mean an acceptable degree of error for the quantity measured given the nature or precision of the measurements. Exemplary degrees of error are within 20-25 percent (%), typically, within 10%, and more typically, within 5% of a given value or range of values. The terms "about" and "approximately" include the recited value being modified; for example, "about 1.5" includes the recited value 1.5, as well as an acceptable degree of error around the recited value 1.5.

Furthermore, in those instances where a convention analogous to "at least one of A, B and C, etc." is used, in general such a construction is intended in the sense of one having ordinary skill in the art would understand the convention (for example, "a system having at least one of A, B and C" would include but not be limited to systems that have A alone, B alone, C alone. A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "from," "to," "up to," "at least," "greater than," "less than," and the like, include the number recited and refer to ranges which can subsequently be broken down into sub-ranges.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

The chemical structures described herein are named according to IUPAC nomenclature rules and include art-accepted common names and abbreviations where appropriate. The IUPAC nomenclature can be derived with chemical structure drawing software programs, such as ChemDraw® (PerkinElmer, Inc.), ChemDoodle® (iChemLabs, LLC) and Marvin (ChemAxon Ltd.). The chemical structure controls in the disclosure to the extent that an IUPAC name is misnamed or otherwise conflicts with the chemical structure disclosed herein.

The chemical structures described herein are also cataloged according to CAS Registry Nos. where appropriate. The chemical structure controls in the disclosure to the extent that an CAS Registry No. is misidentified or otherwise conflicts with the chemical structure disclosed herein.

Experimental Model for Regenerating Spiral Ganglion Neurites

Figure 5:
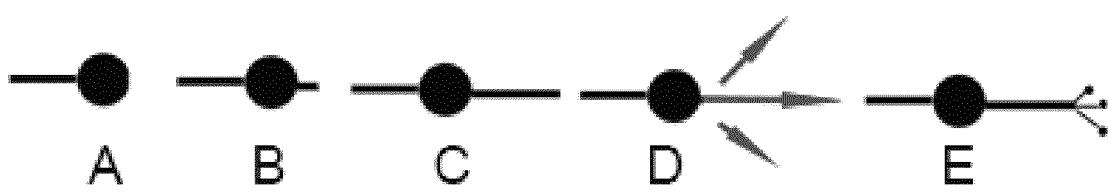
FIG. 5 depicts a model for neurite regeneration of synapses: neuronal survival (subpanel A), neurite initiation (subpanel B); neurite elongation (subpanel C); neurite pathfinding (subpanel D); and synaptogenesis (subpanel E).

The screening procedures disclosed herein considers the problem of spiral ganglion neuron-target reconnection as a sequence of five general steps, wherein not all of which are envisioned as being stimulated by just one type or class of compounds. First, the neurons must survive the insult (FIG. 5A). Second, there must be the "breaking of the sphere" in which the neurite is initiated (FIG. 5B). Third, the neurite must elongate (FIG. 5C). Fourth. the neurite must find its way towards its target (FIG. 5D). Fifth, the neurite ultimately becomes synaptically engaged with the hair cell (FIG. 5E). In the case of PTS, all steps may apply. But in the case of TTS, if the neurites have not had time to retract significantly, elongation can become paramount.

Screening Assay for Identifying Compounds Effective on Spiral Ganglion Neurons.

The in vitro phenotypic screen for spiral ganglion neurons is designed to identify both survival promoting and neurite promoting compounds. The screening procedure focuses on the survival, neurite initiation and neurite elongation steps of the experimental model (FIG. 5A-C). The screening procedure has already been successful in identifying a class of compounds that stimulate the growth of spiral ganglion neurites in vitro. Newborn mouse pups served as a source for preparing primary cultures of the spiral ganglia from 16 cochleas. From these cochleas, 192 cultures in a 384 well plate that enables screening of 45 compounds and 3 controls for each dissection. The screening assay is quite robust, enabling throughput capability significantly higher than in past in vitro spiral ganglion studies.

Figure 6:
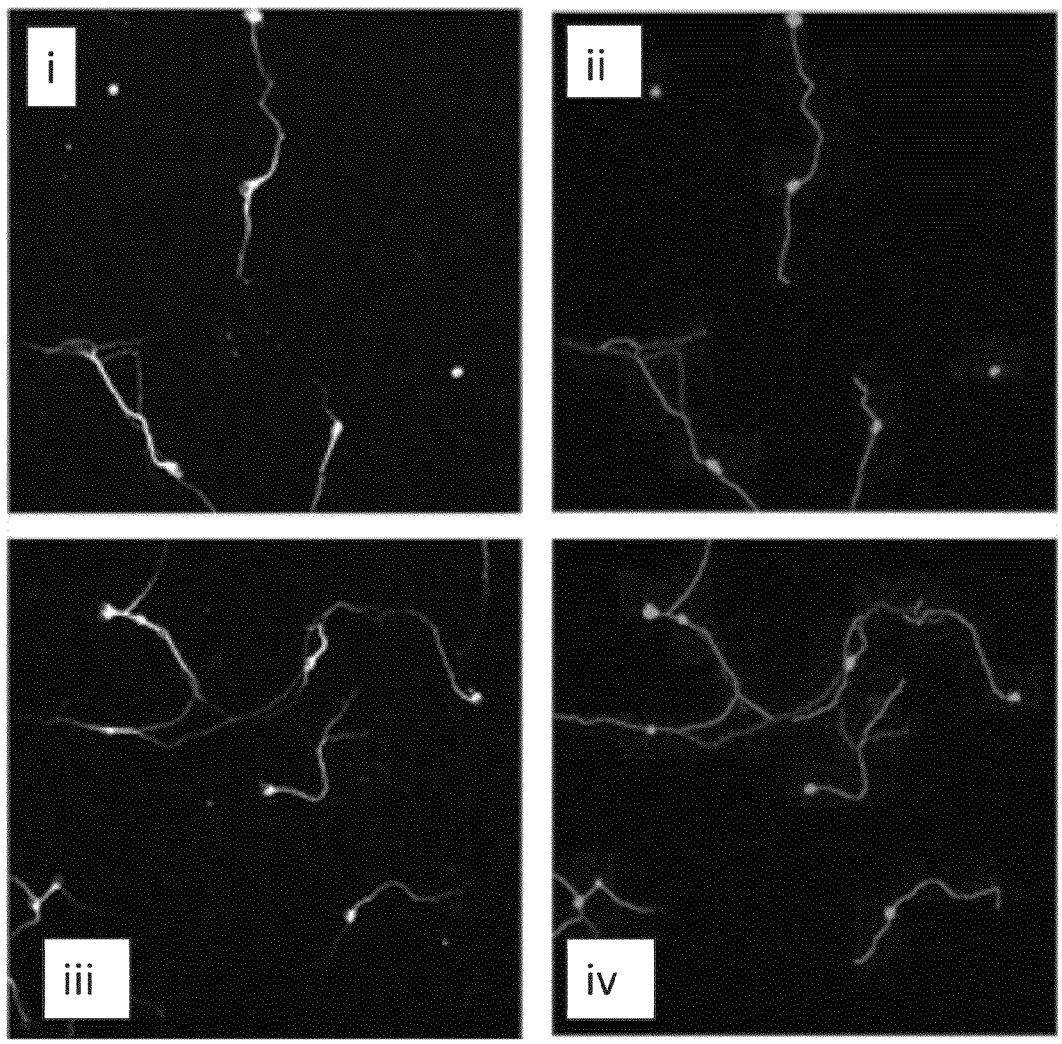
FIG. 6 shows two examples of automatically imaged fields of a spiral ganglion culture (subpanels (i) and (iii)) and the automatic detection of neurons (circles) and neurites (lines) in these fields (subpanels (ii) and (iv)) by the software HCA vision.

The screening approach preferably uses automated imaging and computer assisted data analysis. FIG. 6 shows two examples of neurites and neurons identified by the software HCA Vision. Neurite length in cultures under various conditions can be analyzed by hand imaging; however, neurite measurements in three experiments can require at least 3 months of labor-intensive analysis (FIG. 7A).

Similar experiments performed using automated imaging and measurement methods typically require less than 4 hours for analysis (FIG. 7B). Populations of neurites are measured and graphed as cumulative percent histograms of neurite length. In these graphs, a shift to the right means that the population had longer neurites. The automated imaging provided results similar to those found by hand: the rank order of the neurite lengths under the four different conditions was the same. It is clear from these graphs that the growth of neurites can be stimulated in culture and the results are reproducible from experiment to experiment.

The Rho kinase inhibitor H1152 was tested for its effects on neurite lengths and compared to other Rho kinase inhibitors as a means of validating the reproducibility of the in vitro screening assay. Rho kinase is an enzyme involved in the regulation of the cytoskeletal protein actin. The H1152 compound has the IUPAC name: 4-methyl-5-{[(2S)-2-methyl-1,4-diazepan-1-yl]sulfonyl}isoquinoline (CAS Registry No. 451462-58-1) and is illustrated by formula (I):

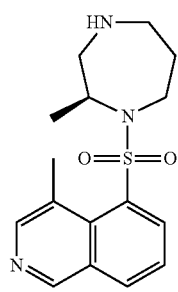

Figure 7:
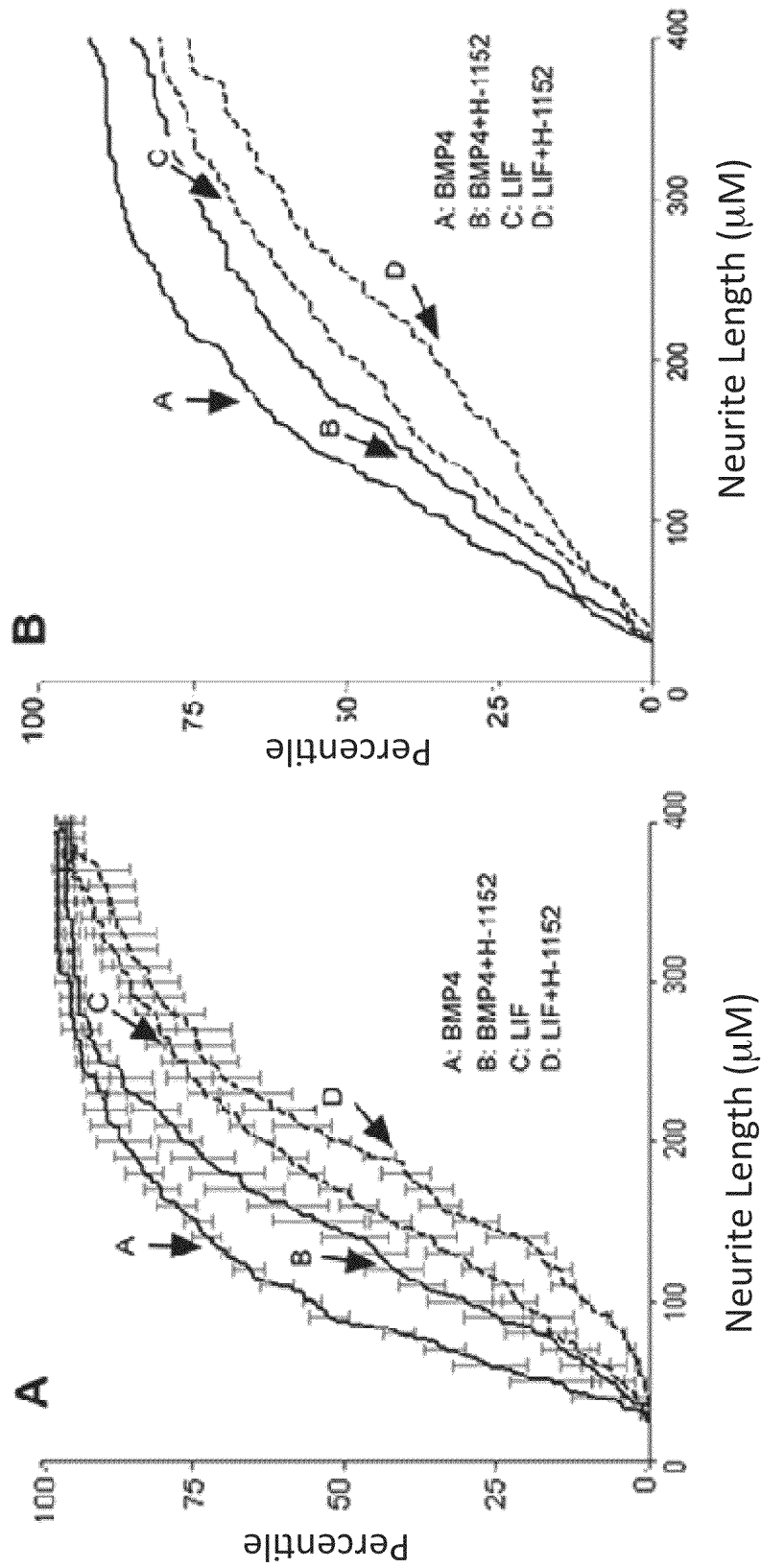
FIG. 7A depicts cumulative percent histograms of neurite lengths in spiral ganglion cultures exposed to BMP4 (curves A), BMP4+H1152 (Curves B), LIF (curves C), and LIF+H1152 (curves D). The plot depicts the averages of three experiments in which the neurites were imaged and measured by hand.
FIG. 7B depicts cumulative percent histograms of neurite lengths in spiral ganglion cultures exposed to BMP4 (curves A), BMP4+H1152 (Curves B), LIF (curves C), and LIF+H1152 (curves D). The plot depicts one experiment that was automatically imaged and measured with Cellomics Software.
Figure 8:
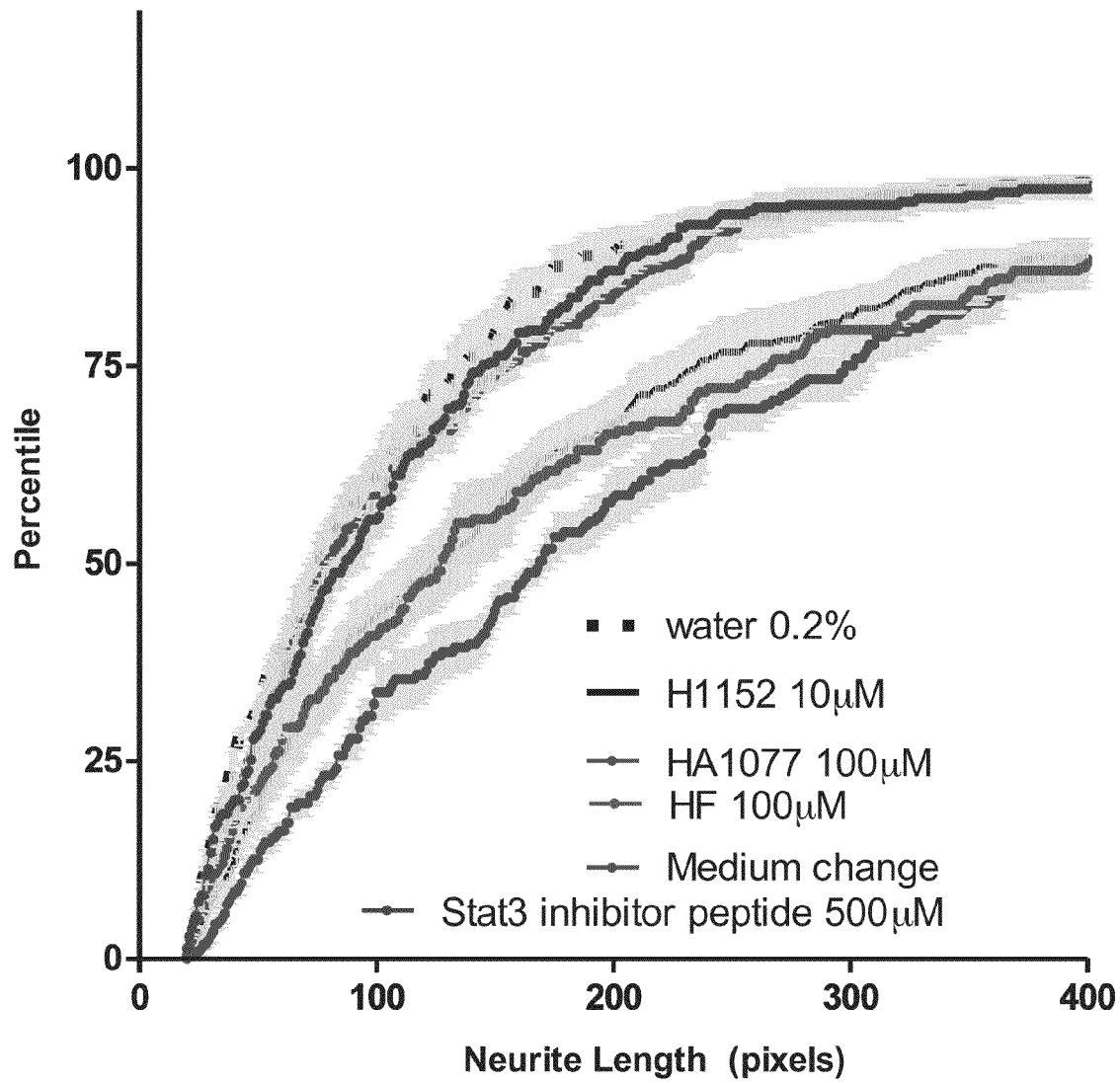
FIG. 8 depicts cumulative percent histograms of neurite lengths in spiral ganglion cultures exposed to media containing a negative control substance (water, media change or an irrelevant inhibitor stat 3 inhibitor peptide) or with media containing one of H1152, HA1077 or HF at the indicated concentrations. Neurite length is automatically measured by HCA Vision from the images of the cultures and the length is depicted in pixels.

The H1152 compound could stimulate neurite length when neurite cultures were contacted with the compound under culture conditions that included BDNF and NT3BMP4 or culture conditions that include BDNF, NT3, LIF (FIG. 7). Other Rho kinase inhibitors—Fasudil (HA1077) and Hydroxyl Fasudil (HF) also stimulated neurite length in a similar way, albeit at higher concentration. However, media change, or an irrelevant inhibitor did not increase neurite length (FIG. 8). These studies demonstrated a very reproducible assay for neurite length that could be performed semi-automatically in comparatively little time.

Figure 9:
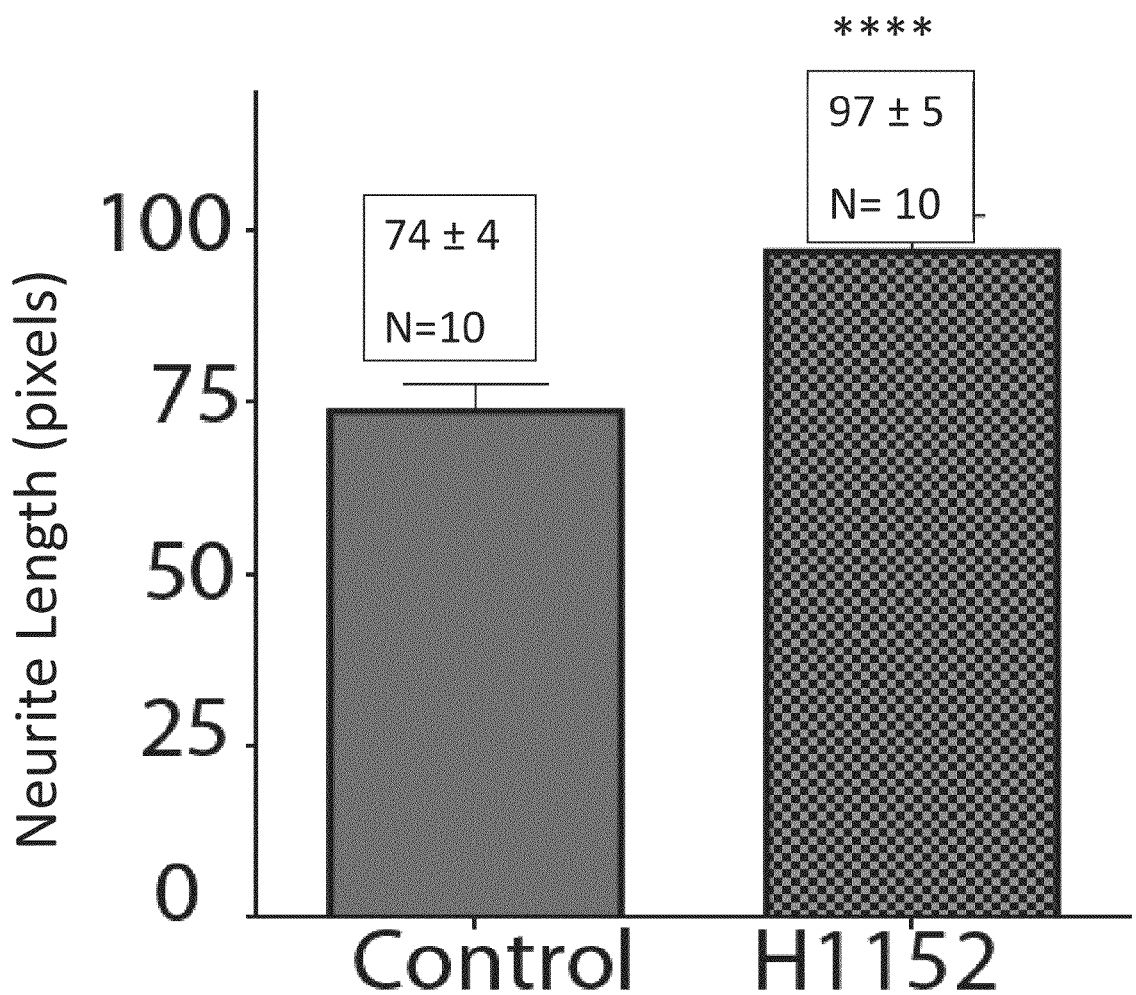
FIG. 9 depicts the medial neurite length (pixels) for population of neurites in spiral ganglion cultures contacted with media containing a negative control substance (water) or with media containing H1152. The data represents the averages often separate experiments. Statistical data key: ****, $p<0.00001$

The screen utilizes H1152 as a positive control. FIG. 9 shows the median neurite lengths from 10 experiments in cultures treated with water or H1152. In all experiments in all assays H1152 increased neurite lengths, once again demonstrating the reproducibility of results across experiments.

Figure 10:
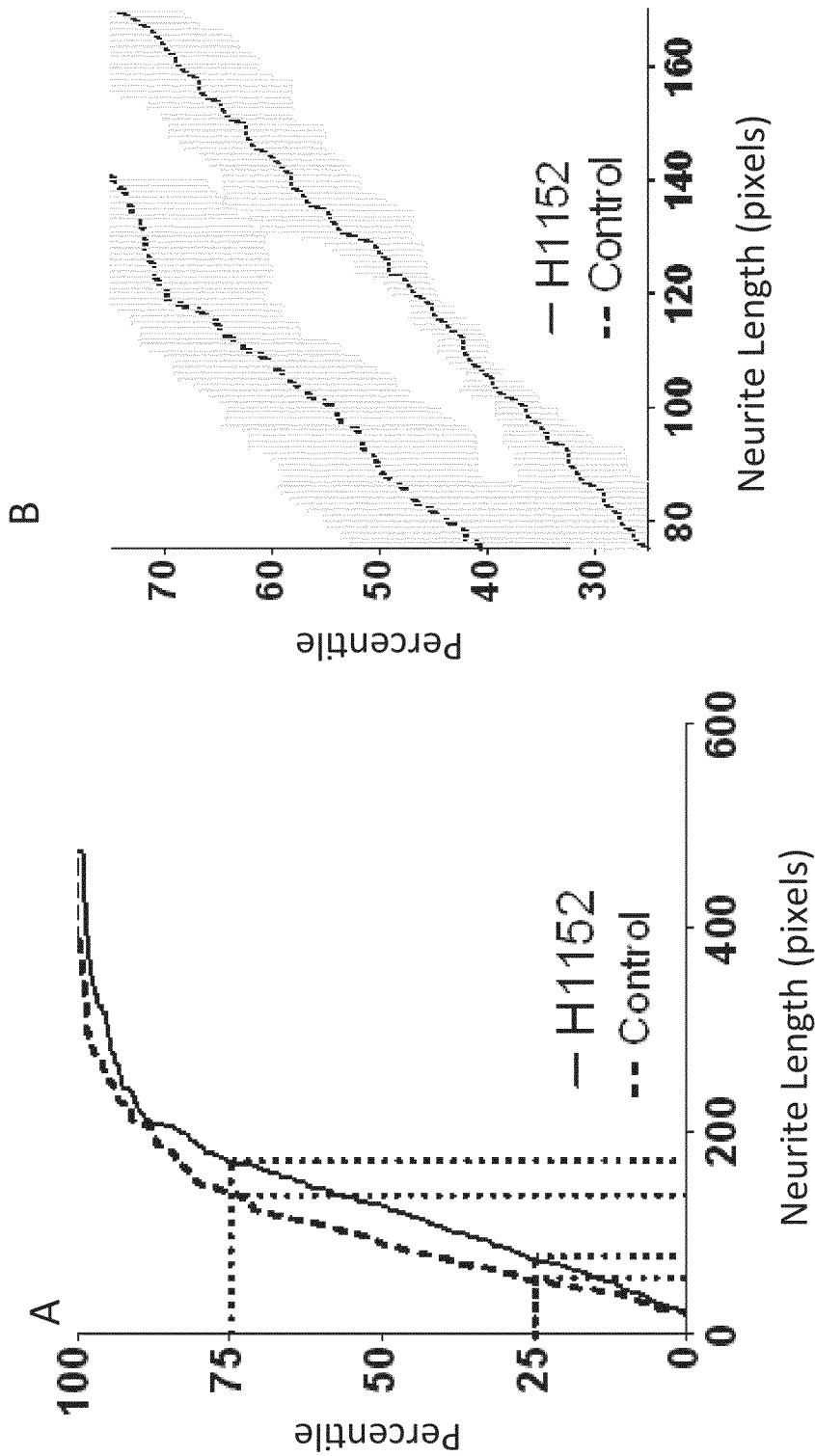
FIG. 10A depicts an example of how neurite length data is graphed for a complete cumulative percent histogram of neurite lengths from cultures contacted with media containing water (control) or H1152.
FIG. 10B depicts an example neurite length data graphed for the region containing the $25^{th}$ to the $75^{th}$ percentile of the cumulative percent histogram of neurite lengths from cultures contacted with media containing water (control) or H1152.
Figure 11:
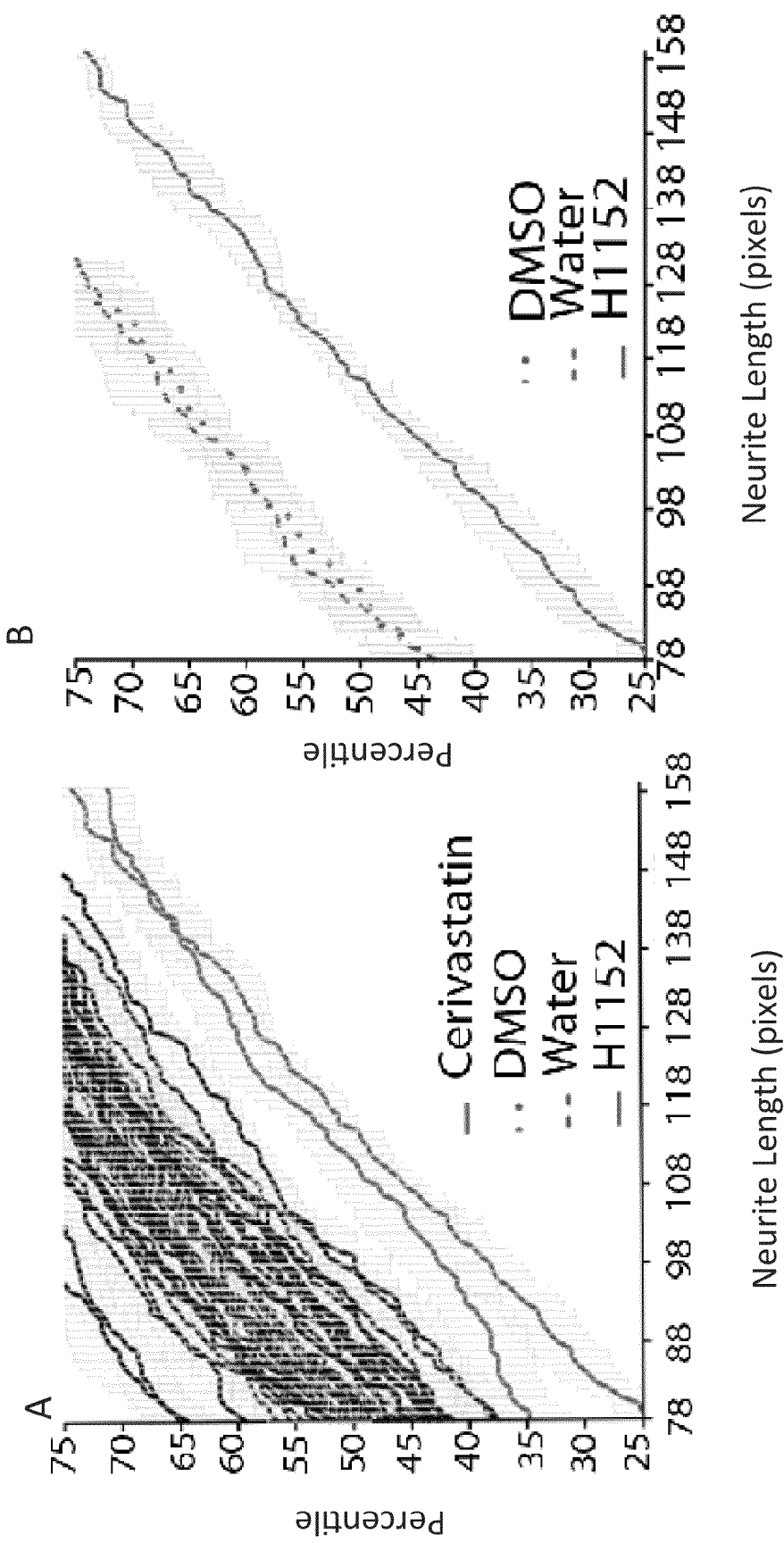
FIG. 11A depicts an example of the neurite length data acquired in an actual screen in which Cerivastatin was identified as a neurite elongation agent. Cumulative percent histograms of the region containing the $25^{th}$ to the $75^{th}$ percentile of the positive control are plotted.
FIG. 11B depicts an example of the neurite length data acquired in an actual screen for cells contacted with culture media containing the negative (DMSO, water) and positive (H1152) controls of the experiment depicted in FIG. 11A.
Figure 12:
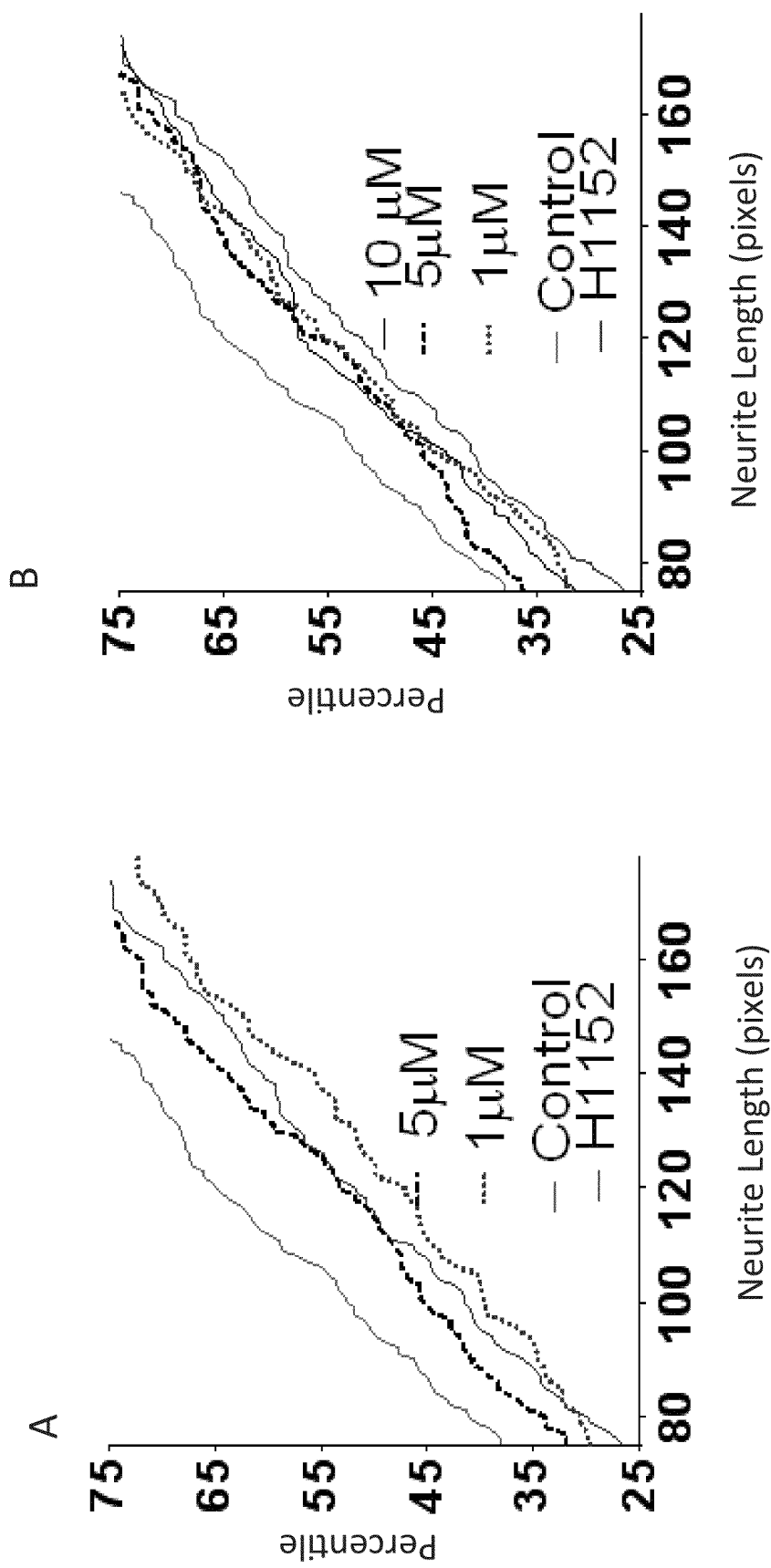
FIG. 12A depicts a neurite length dose response graph for Cerivastatin. Cumulative percent histograms containing the $25^{th}$ to the $75^{th}$ percentile of the positive control (H1152) are plotted. The lowest effective dose in this experiment for the statin was 1 µM.
FIG. 12B depicts a neurite length dose response graph for Fluvastatin. Cumulative percent histograms containing the $25^{th}$ to the $75^{th}$ percentile of the positive control (H1152) are plotted. The lowest effective dose in this experiment for the statin was 1 µM.
Figure 13:
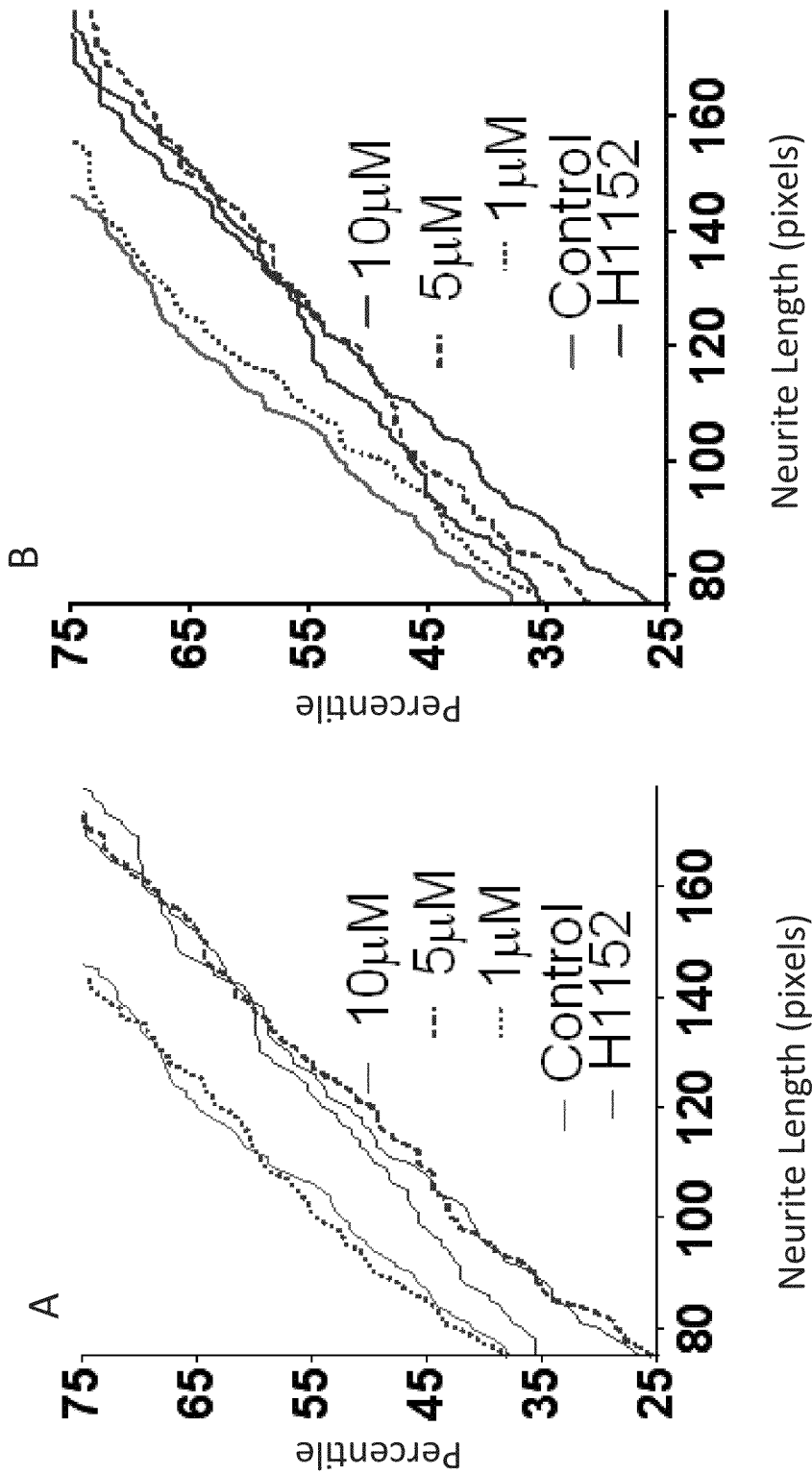
FIG. 13A depicts a neurite length dose response graph for Simvastatin. Cumulative percent histograms containing the $25^{th}$ to the $75^{th}$ percentile of the positive control (H1152) are plotted. The lowest effective dose in this experiment for the statin was 5 µM.
FIG. 13B depicts a neurite length dose response graph for Lovastatin. Cumulative percent histograms containing the $25^{th}$ to the $75^{th}$ percentile of the positive control (H1152) are plotted. The lowest effective dose in this experiment for the statin was 5 µM.
Figure 14:
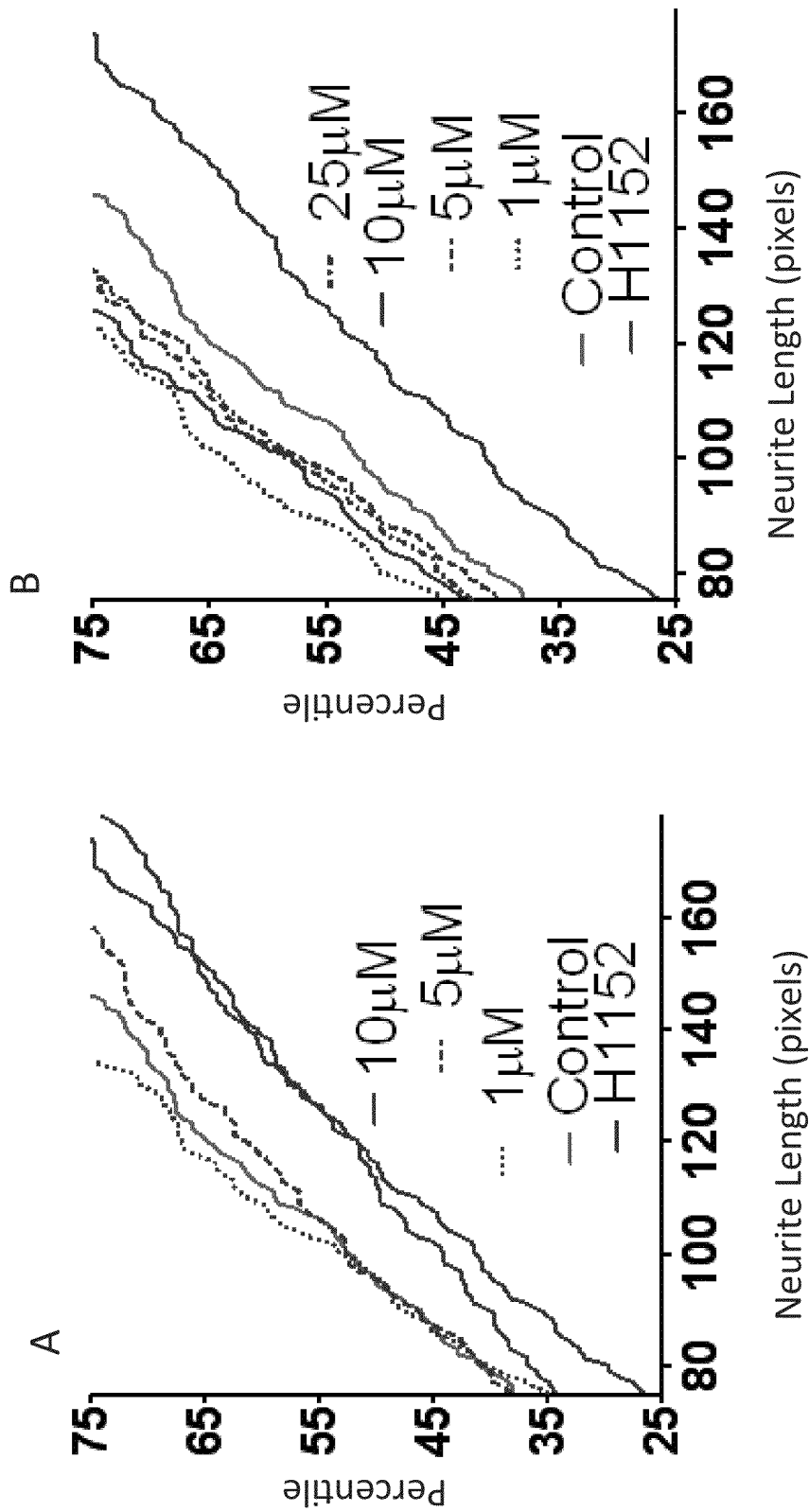
FIG. 14A depicts a neurite length dose response graph for Atorvastatin. Cumulative percent histograms containing the $25^{th}$ to the $75^{th}$ percentile of the positive control (H1152) are plotted. The lowest effective dose in this experiment for Atorvastatin was 10 µM.
FIG. 14B depicts a neurite length dose response graph for Pravastatin. Cumulative percent histograms containing the $25^{th}$ to the $75^{th}$ percentile of the positive control (H1152) are plotted. Pravastatin was ineffective up to the highest dose tested, 25 µM.
Figure 15:
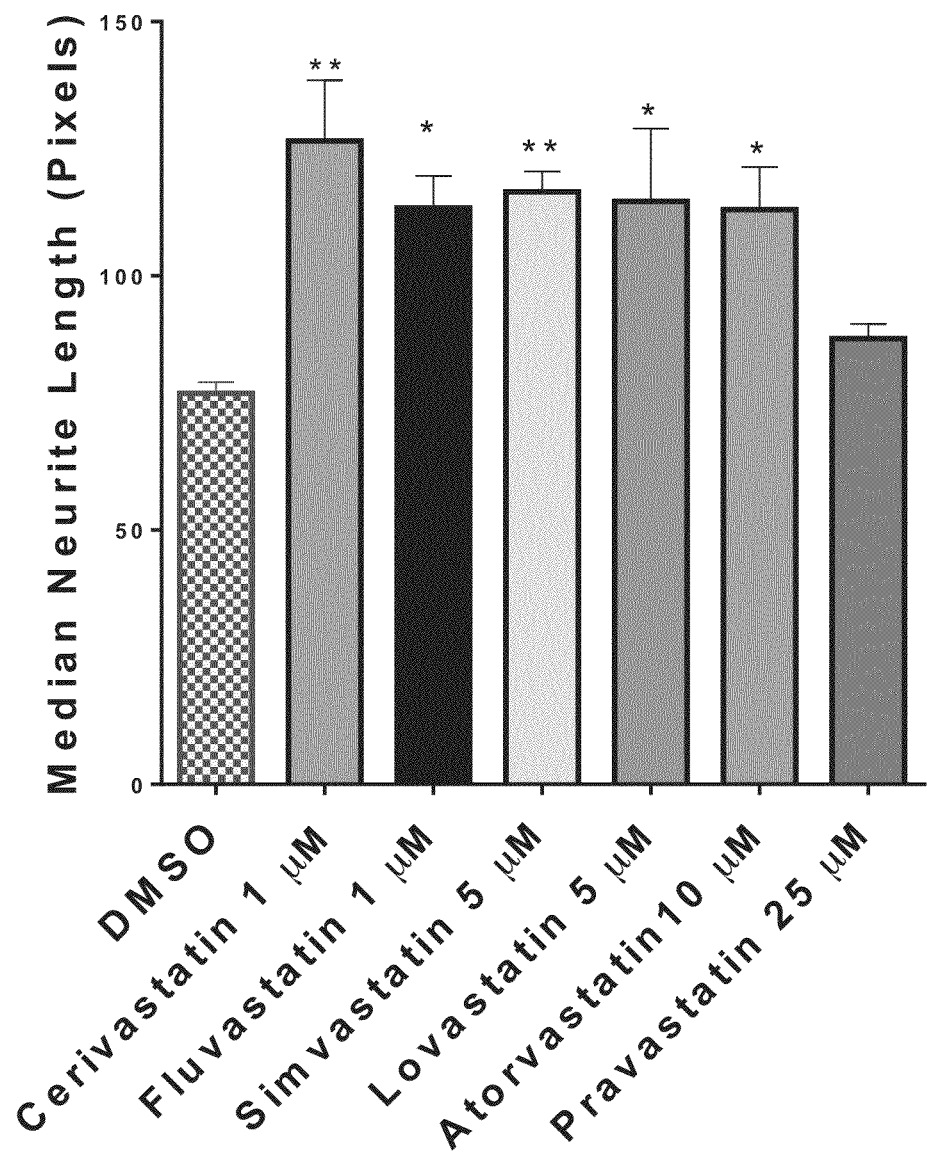
FIG. 15 depicts the median neurite lengths of the negative control (DMSO) and the statins at their lowest effective doses. Pravastatin was ineffective up to 25 µM. All other statins demonstrated statistically significant differences in neurite lengths as compared to the DMSO control. Statistical key: *, $p<0.05$; **, $p<0.01$.

For the screen, only an enlargement the region between $25^{th}$ and $75^{th}$ percentile was plotted because that is where the biggest differences could be detected (FIG. 10A-B). A compound screen on spiral ganglion neurons was performed by evaluating 480 compounds of the NIH Clinical Collection, a library of molecules that have a history of use in clinical trials unrelated to cochlear function. FIG. 11 shows an example of part of the data from one dissection on which all the histograms from one dissection were plotted on the same axes. Some of the cultures have very short neurites, and those are usually undergoing cell death. Most of the histograms overlie the negative controls (water, DMSO) (FIGS. 11A-B). The statin Cerivastatin stimulated neurite growth as well as H1152 (FIG. 11A).

Since the compound Cerivastatin was well characterized from previous clinical trials, the structure of the compound was used to screen compounds having similar structure for their effect on stimulating neurite growth. Only the $50^{th}$ percentile neurite lengths from these dose response curves at the lowest effective dose were plotted. Referring to FIGS. 12-15, all but one had neurite lengths that were different from the DMSO control, although their lowest effective doses were different. These compounds are actually drugs that are used for a purpose other than neurite regeneration. As these compounds inhibit the rate-limiting step in cholesterol synthesis, the accepted use for these drugs is to lower blood cholesterol levels.

Exemplary statins useful for stimulating neurite growth from spiral ganglion neurons of cochlea include the compounds identified in Table I. In the screening assay the lowest effective dose differed among the statins as follows: Cetivastatin (1 µM), Fluvastatin (1 µM), Simvastatin (5 µM), Lovastatin (5 µM), Atorvastatin (10 µM). In a separate experiment, Mevastatin stimulated neurite growth at the lowest effective dose of 5 µM. Pravastatin did not function to stimulate neurite growth in this assay up to 25 µM. (FIGS. 12-15).

TABLE I

| Exemplary Statins Effective for Stimulating Neurite Growth | | |
|---|---|---|
| Compound Structure (Formula) | IUPAC Name (Common Name) | CAS Reg. No. |
| (Structure II) | 3R,5S,6E)-7-[4-(4-fluorophenyl)-5-(methoxymethyl)-2,6-bis(propan-2-yl)pyridin-3-yl]-3,5-dihydroxyhept-6-enoic acid (Cerivastatin) | 145599-86-6 |

TABLE I-continued

Exemplary Statins Effective for Stimulating Neurite Growth

| Compound Structure (Formula) | IUPAC Name (Common Name) | CAS Reg. No. |
|---|---|---|
| (III) | (3S,5R,6E)-7-[3-(4-fluorophenyl)-1-(propan-2-yl)-1H-indol-2-yl]-3,5-dihydroxyhept-6-enoic acid (Fluvastatin) | 93957-54-1 |
| (IV) | (1S,3R,7S,8S,8aR)-8-{2-[(2R,4R)-4-hydroxy-6-oxooxan-2-yl]ethyl}-3,7-dimethyl-1,2,3,7,8,8a-hexahydronaphthalen-1-yl 2,2-dimethylbutanoate (Simvastatin) | 79902-63-9 |
| (V) | (3R,5R)-7-[(1S,2S,8S,8aR)-2-methyl-8-{[(2S)-2-methylbutanoyl]oxy}-1,2,6,7,8,8a-hexahydronaphthalen-1-yl]-3,5-dihydroxyheptanoic acid (Mevastatin) | 73573-88-3 |
| (VI) | (1S,3R,7S,8S,8aR)-8-{2-[(2R,4R)-4-hydroxy-6-oxooxan-2-yl]ethyl}-3,7-dimethyl-1,2,3,7,8,8a-hexahydronaphthalen-1-yl (2S)-2-methylbutanoate (Lovastatin) | 75330-75-5 |

TABLE I-continued

Exemplary Statins Effective for Stimulating Neurite Growth

| Compound Structure (Formula) | IUPAC Name (Common Name) | CAS Reg. No. |
| --- | --- | --- |
| 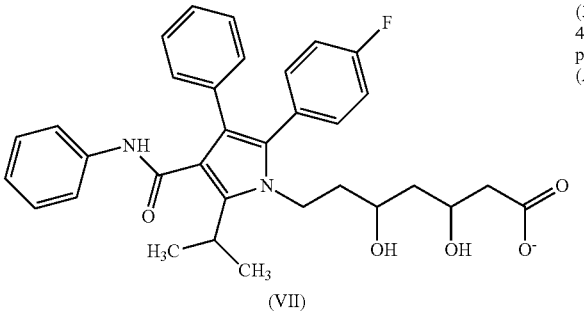 (VII) | (3R,5R)-7-[2-(4-fluorophenyl)-3-phenyl-4-(phenylcarbamoyl)-5-(propan-2-yl)-1H-pyrrol-1-yl]-3,5-dihydroxyheptanoic acid (Atorvastatin) | 134523-00-5 |

Figure 16A:
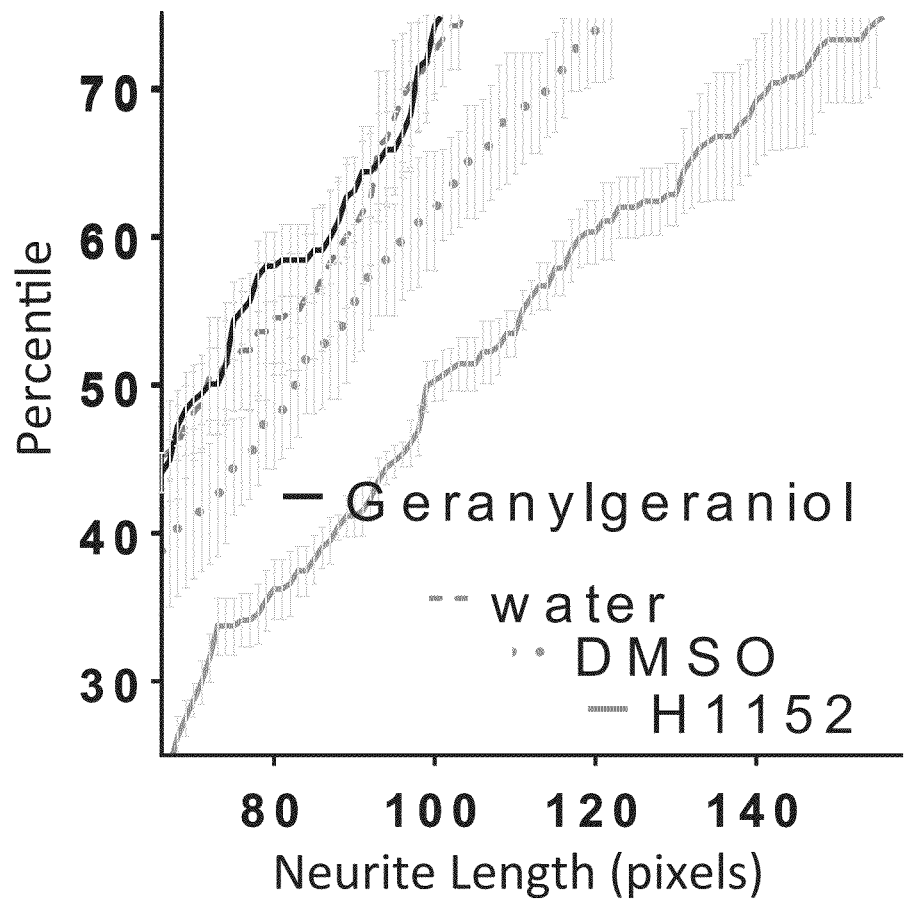
FIG. 16A depicts cumulative percent histograms containing the $25^{th}$ to the $75^{th}$ percentile of the positive control (H1152) of cultures treated with media containing geranylgeraniol (10 µM). Cultures treated with media containing DMSO served as the negative control. Each point is the average of 4 replicate cultures.
Figure 16B:
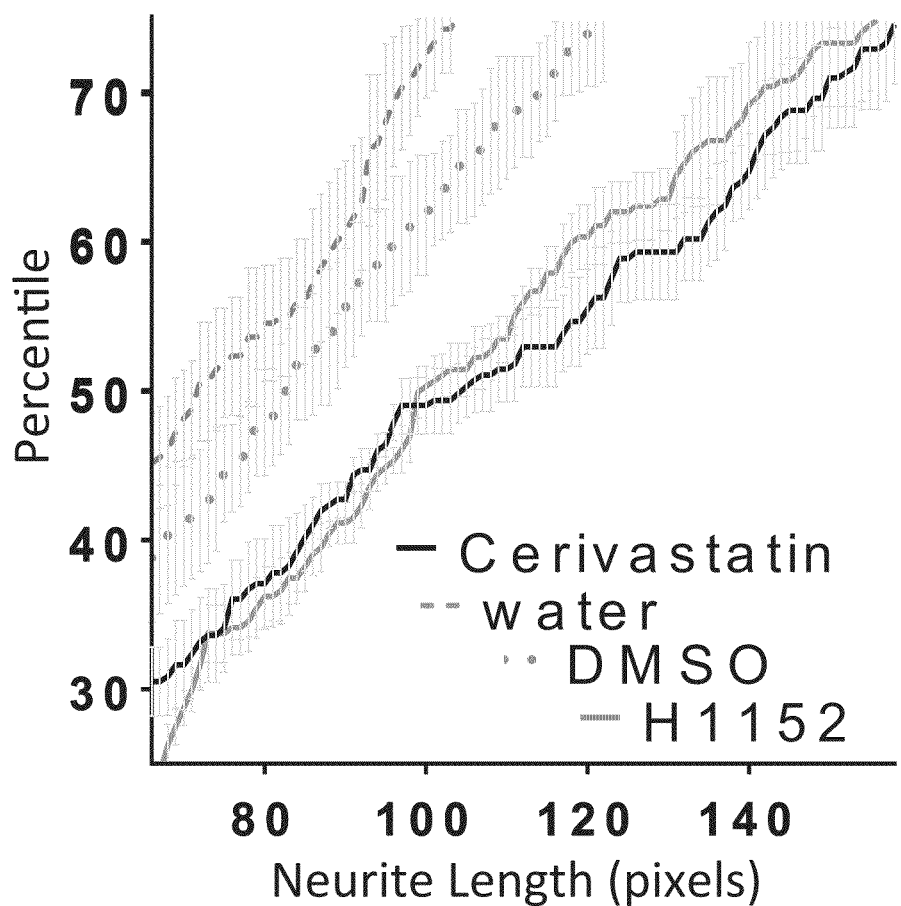
FIG. 16B depicts cumulative percent histograms containing the $25^{th}$ to the $75^{th}$ percentile of the positive control (H1152) of cultures treated with media containing Cerivastatin (10 µM). Cultures treated with media containing DMSO served as the negative control. Each point is the average of 4 replicate cultures.
Figure 16C:
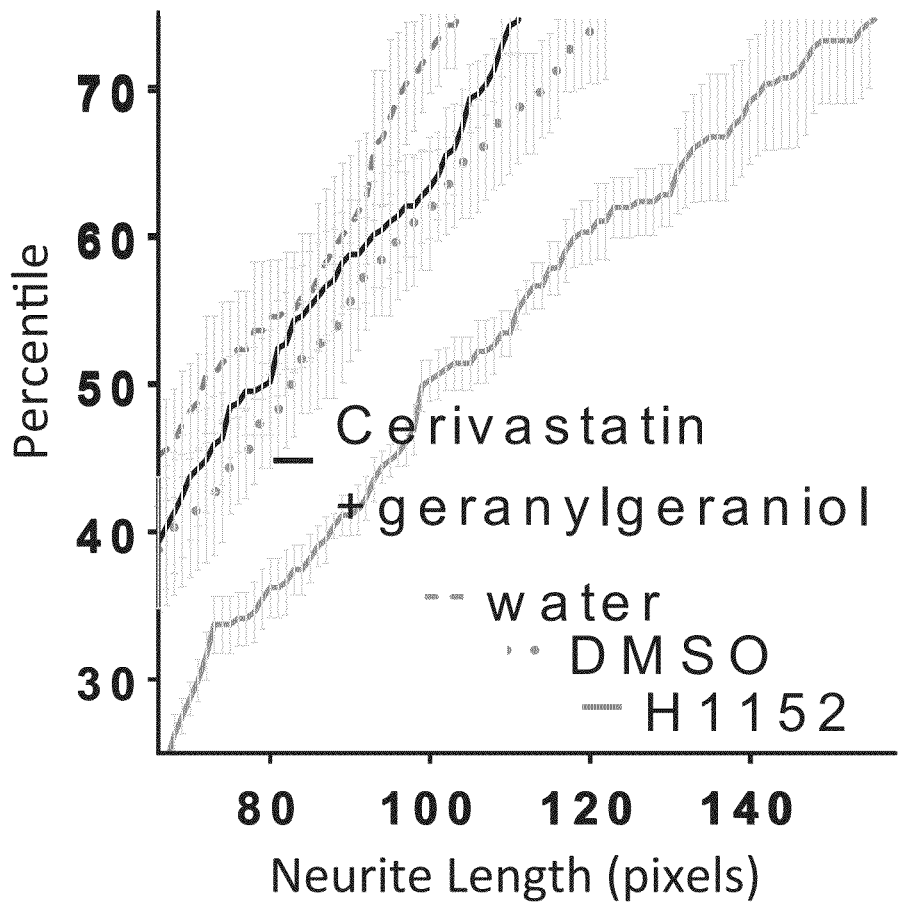
FIG. 16C depicts cumulative percent histograms containing the $25^{th}$ to the $75^{th}$ percentile of the positive control (H1152) of cultures treated with media containing Cerivastatin (10 µM) and geranylgeraniol (10 µM). Cultures treated with media containing DMSO served as the negative control. Each point is the average of 4 replicate cultures.
Figure 17A:
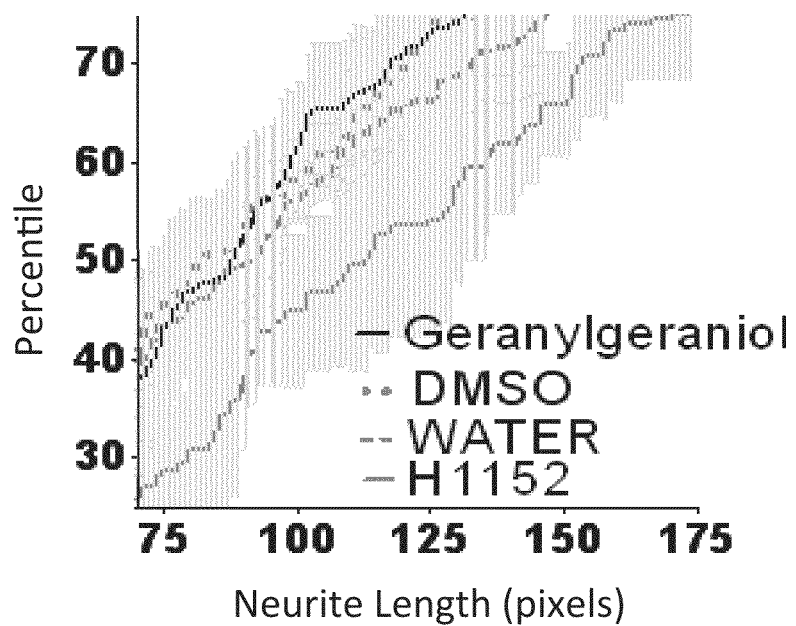
FIG. 17A depicts cumulative percent histograms containing the $25^{th}$ to the $75^{th}$ percentile of the positive control (H1152) of cultures treated with media containing geranylgeraniol (10 µM). Cultures treated with media containing DMSO served as the negative control. Each point is the average of 4 replicate cultures.
Figure 17B:
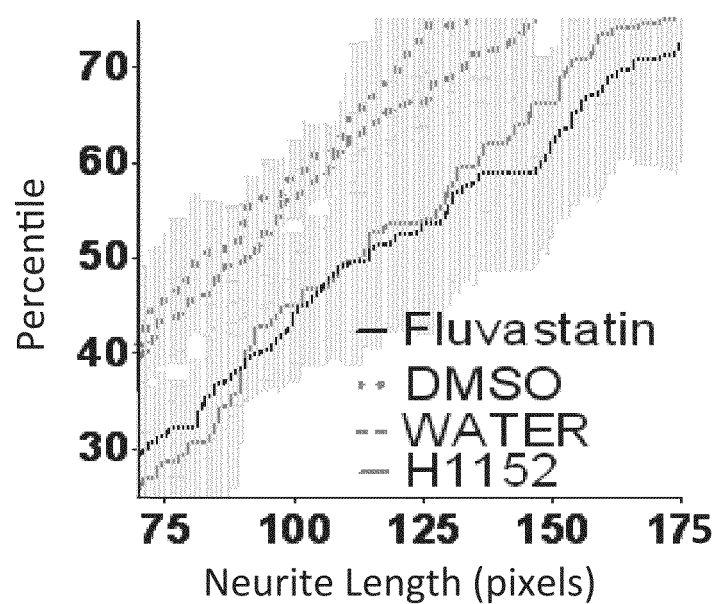
FIG. 17B depicts cumulative percent histograms containing the $25^{th}$ to the $75^{th}$ percentile of the positive control (H1152) of cultures treated with media containing Fluvastatin (5 µM). Cultures treated with media containing DMSO saved as the negative control. Each point is the average of 4 replicate cultures.
Figure 17C:
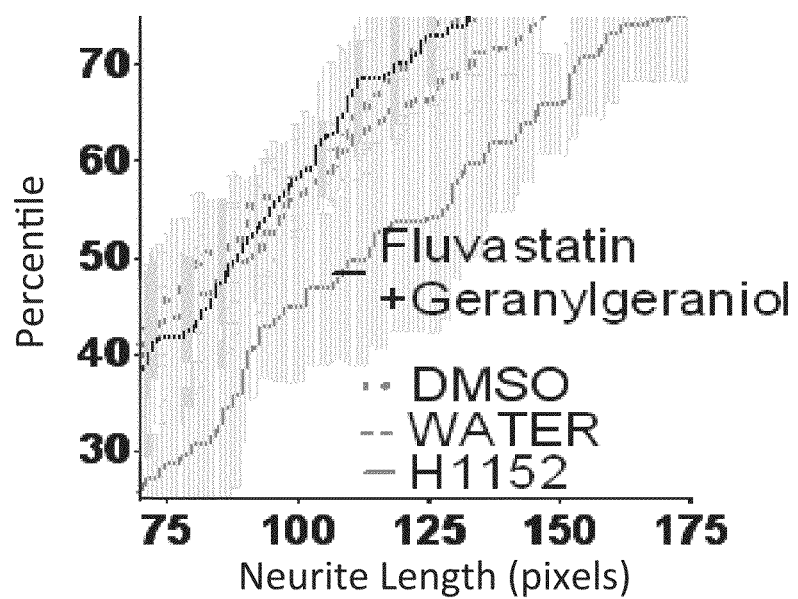
FIG. 17C depicts cumulative percent histograms containing the $25^{th}$ to the $75^{th}$ percentile of the positive control (H1152) of cultures treated with media containing Fluvastatin (5 µM) and geranylgeraniol (10 µM). Cultures treated with media containing DMSO served as the negative control. Each point is the average of 4 replicate cultures.

To discern potential molecular targets for the action of Cerivastatin, several compounds were evaluated to determine whether the stimulatory effect of Cerivastatin on neurite elongation could be blocked when populations of neurites were contacted with media containing both Cerivastatin and one of the compounds under evaluation. FIG. 16 demonstrates that populations of neurites contacted with media containing Cerivastatin at 10 µM increased neurite length (FIG. 16B), whereas populations of neurites contacted with media containing both Cerivastatin and geranylgeraniol effectively blocked the stimulatory effect of Cerivastatin on neurite length (FIG. 16C). A similar effect of geranylgeraniol was observed when Fluvastatin was used to increase neurite length (FIG. 17B). Without the claimed subject matter being limited to any particular physiological mechanism, Cerivastatin and other statins may stimulate neurite elongation by blocking production and subsequent post-translational attachment of geranylgeraniol moieties to proteins via geranylgeranylation.

Evaluation of Statins in an Animal Model for PTS

In one embodiment, Fluvastatin provided effective protection by preventing hearing loss in vivo. A testing method with a guinea pig model of PTS was developed for this purpose. Compounds were introduced into the left ear of the subject with a cannula attached to a miniosmotic pump. Because the cannula is physically within the cochlea, it had the possibility of interfering with sound transfer in the cochlea, and thereby interfering with auditory brain response (ABR) measurements. For this reason, the compound was delivered via cannula to the left ear, but tested for its effect in the contralateral ear, taking advantage of the connection between cochlear fluids and the cerebral spinal fluid. Animals were subjected to an sound injury causing PTS. Fluvastatin was delivered in vivo to the left ear at 50 times the concentration that was effective for stimulating neurite growth in vitro and ABRs were evaluated in the contralateral, right cochleas. The experimental protocol was designed to induce PTS, then evaluate the regrowth of spiral ganglion neurites. The compound was first evaluated for the ability to provide a protective effect from hearing loss attributed to high level noise, wherein the compound was delivered at the same time as the noise exposure and for 4 weeks thereafter. ABRs were taken every week for 4 weeks.

Figure 18:
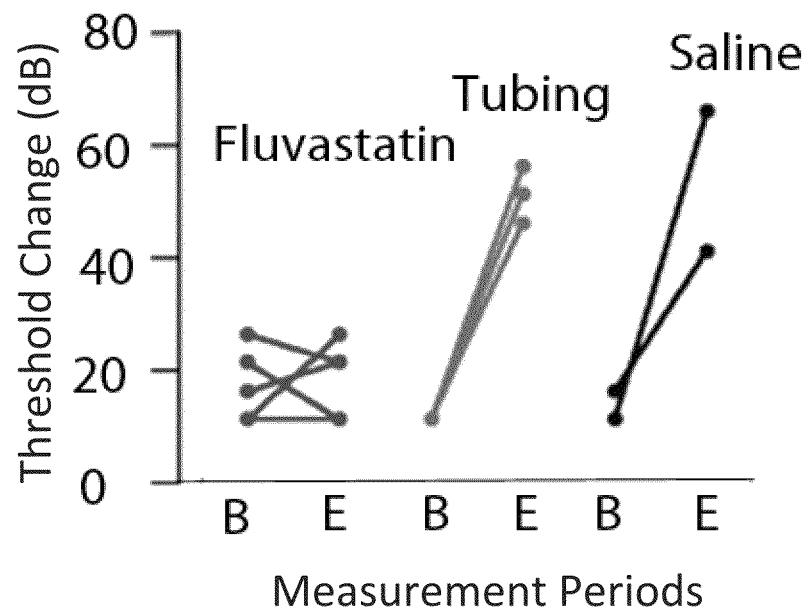
FIG. 18 depicts the effects of Fluvastatin on hearing in PTS noise exposed guinea pigs. Threshold change (dB) is plotted from baseline (B, before noise exposure) to end of study (E, 4 weeks). Using miniosmotic pumps, the left ear was infused with 50 µM Fluvastatin, 250 µL over 28 days, or Saline, or contained tubing with no solution. Hearing was measured in the contralateral ear.
Figure 19:
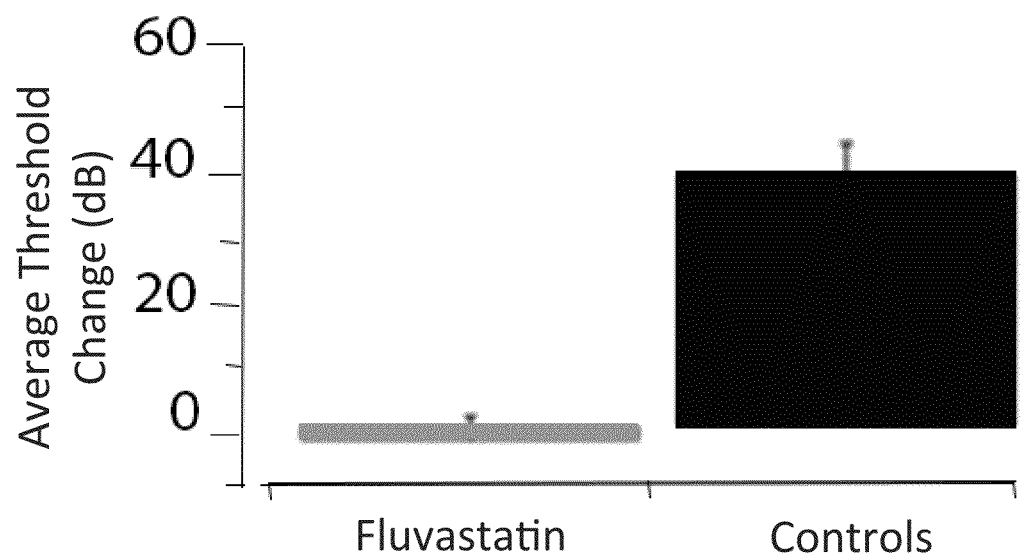
FIG. 19 depicts the averages and standard deviations from the data in FIG. 18. Catheter alone and the results for saline delivery were combined and are represented as controls.

Referring to FIGS. 18 and 19, a permanent threshold shift was observed in the right ear in animals in which the left ear received only saline or a closed off cannula without saline, the controls. Under the conditions tested PTS injury could not be induced in the right cochlea of animals whose left cochleas were treated with Fluvastatin. Without the claimed subject matter being limited by any particular physiological mechanism, Fluvastatin may protect hearing from acute acoustic injury by maintaining the integrity of the hair cells in the cochlea.

This protocol demonstrated that delivery of a compound to one cochlea was effective to evaluate its effects in the opposite cochlea, which was not surgically manipulated in any way. Owing to the limited space in which compounds diffuse, even the delivery of 50 µM compound in 250 µl solution over 4 weeks is a minimal dosage (<500 pmole/day) and helps ensure that whole body toxicity is not an issue when testing the compound. Thus, CSF spread of compounds has been used to advantage in a study of compounds in the ear.

Pharmaceutical Compositions

The present disclosure contemplates pharmaceutical compositions of the disclosed compound(s) for administration to mammals for stimulating neurite growth from spiral ganglion neurons in the inner ear and methods for preventing damage to or treating damage of auditory neurons and/or hair cells of the cochlea following acoustic or toxic insult. In a preferred embodiment, a composition for administration is a pharmaceutical composition, preferably in a single unit dosage form. Pharmaceutical compositions and single unit dosage forms can comprise a prophylactically or therapeutically effective amount of one or more prophylactic or therapeutic agents, and a typically one or more pharmaceutically acceptable carriers or excipients or diluents.

The term "pharmaceutically acceptable" means approved by a regulatory agency of the Federal or a state government (for example, the U.S. Food and Drug Administration) or listed in the U.S. Pharmacopeia or other generally recognized pharmacopeia for use in animals, and more particularly in humans.

The compounds of this invention may exist as a pharmaceutically acceptable salt. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit:risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure.

Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine. N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like, are contemplated as being within the scope of the present invention.

The compounds may be incorporated into pharmaceutical compositions suitable for administration to a subject (such as a patient, which may be a human or non-human). The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result, such as prevention or protection from hearing loss. Typically, since a prophylactic dose is used in subjects prior to or at an earlier stage of disease, the prophylactically effective amount will be less than the therapeutically effective amount.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water, DMSO or the aforementioned oils can be preferred carriers when the pharmaceutical composition is administered into the ear canal. Examples of suitable pharmaceutical carriers are described in "Remington's Pharmaceutical Sciences" by E. W. Martin. Pharmaceutical compositions can, but need not, comprise one or more active or inactive ingredients that are not necessarily considered pharmaceutically acceptable to current practitioners in the art.

Methods of treatment may include any number of modes of administering the composition of the present invention. Modes of administration for inner ear may include aqueous, lipid, oily or other solutions, emulsions such as oil-in-water emulsions, liposomes, aqueous or oily suspensions, and syrups. In the pharmaceutical composition, the agent may also be dispersed in a microparticle, e.g., a nanoparticulate composition.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

The disclosure further encompasses administration of pharmaceutical compositions and single unit dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The formulation should suit the mode of administration. In a preferred embodiment, the pharmaceutical compositions and single unit dosage forms are sterile and prepared in a form suitable for administration to a subject, preferably an animal subject, more preferably a mammalian subject, and most preferably a human subject. Besides humans, preferred animal subjects include horses, birds, cats, dogs, rats, hamsters, mice, guinea pigs, cows, and pigs.

Examples of dosage forms include, but are not limited to: gels, dispersions; ointments; liquid dosage forms suitable for inner ear canal mucosa or round window administration to a patient, including suspensions (for example, aqueous or non-aqueous liquid suspensions, oil-in-water emulsions, or a water-in-oil liquid emulsions), solutions; and sterile solids (for example, crystalline or amorphous solids or granular forms) that can be reconstituted to provide liquid dosage forms suitable for ear canal administration to a patient.

The composition, shape, and type of dosage forms of a preparation of the described compounds will typically vary depending on their use. For example, a dosage form used in the acute treatment of for stimulating neurite growth from spiral ganglion neurons in the inner ear or for preventing damage to or treating damage of auditory neurons and/or hair cells of the cochlea following acoustic insult may contain larger amounts of one or more of a preparation of the disclosed compounds than a dosage form used in the chronic treatment of the same disease. Also, the therapeutically effective dosage form may vary among different types of diseases or disorders. Similarly, an ear canal or round window dosage form may contain smaller amounts of one or more of the active than an oral dosage form used to treat the same disease or disorder. These and other ways in which specific dosage forms encompassed by this invention will vary firm one another will be readily apparent to those skilled in the art. See, e.g., Remington's Pharmaceutical Sciences, 18th ed., Mack Publishing, Easton Pa. (1990).

Generally, the ingredients of compositions comprising a preparation of the disclosed compounds are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the certain ear canal or round window dosage forms are solid and prepared under anhydrous conditions with anhydrous ingredients, as described in detail in the sections above. However, the scope of the invention extends beyond anhydrous, solid oral dosage forms. As such, further forms are described herein.

Typical ear canal or round window dosage forms can be prepared by combining the active ingredient(s) (that is, a preparation of the disclosed compound(s)) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Examples of excipients that can be used in ear canal or round window dosage forms of the invention include, but are not limited to lubricants. Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, con oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The amount of the composition in the methods of the invention which will be effective for stimulating neurite growth from spiral ganglion neurons in the inner ear and/or for preventing damage to or treating damage of auditory neurons and/or hair cells of the cochlea following acoustic or toxic insult will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the hearing loss, as well as age, body, weight, response, and the past medical history of the patient. Effective doses may be extrapolated from dose-response curves derived from in vitro or animal model test systems.

Typical dosage forms for administration in the disclosed comprise a composition as disclosed herein in an amount within the range of from about 0.001 mg to about 20 mg of the disclosed compounds per day, about 0.10 mg to about 10 mg of the disclosed compounds per day, or about 1.0 mg to about 2.0 mg of the disclosed compounds per day given as a single once-a-day dose or as divided doses throughout the day. Particular dosage forms of the invention have incremental variations from about 0.001, 0.01, 0.1, 0.2, 0.25, 0.3, 0.5, 0.75, 1.0, 2.0, 2.5, 3.0, 5.0, 7.5, 10.0, 15.0, 20.0, 25.0, 40.0, 50.0, 60.0, 75.0, 100, 125, 150, 175, and 200 mg of the disclosed compounds, as well as incremental dosage variations thereof.

Exemplary dosage forms of the invention having a liquid formulation include 1, 3, 5, 7.5, 10, 15, 20, 50, 75, and 100 µl of a liquid composition of the disclosed compounds having a concentration ranging from about 0.01 mg/ml to about 500 mg/ml. The preferred concentrations of such liquid compositions will depend upon the dissolution characteristics of the medium, which will determine the upper limit of pharmaceutically acceptable concentrations of the disclosed compounds in such compositions. Consequently, alternative, pharmaceutically acceptable, concentrations of the disclosed compounds in liquid compositions that are lower, as well as higher, than that stated herein are also contemplated by the present invention.

In the case of liquid dosage forms, suitable concentrations of the disclosed compounds are suspended or dissolved in pharmaceutically acceptable carrier media, such as water, saline, and the like. Furthermore, suitable concentrations of the disclosed compounds are suspended or dissolved under physiologically and physiochemically appropriate conditions.

Exemplary doses of a composition of the disclosed compounds include microgram or milligram amounts of the disclosed compound(s) per kilogram of subject or sample weight. For example, a therapeutically effective amount of a compound disclosed herein may be from about 0.2 mg/kg to about 5 mg/kg, including incremental dosage variations within this range.

As explained in the disclosure, certain of the disclosed compounds differ in their hydrophobicity, thereby rendering them insoluble, slightly soluble, moderately soluble, very soluble or highly soluble in a particular solvent system, such as aqueous solvents (for example, water or saline) or solvent systems (for example, water/DMSO or saline/DMSO). To the extent that solubility presents a barrier to providing adequate ADME properties for the delivery system or route of administration for certain of the disclosed compounds, particle size reduction of the disclosed compounds to increase solvent-accessible surface area and solvation potential can improve solubility of the disclosed compounds having hydrophobic properties. Methods, techniques and instrumentation are known in the art for achieving particle size reduction (for example, micronization) can be useful for achieving particle size reduction for the disclosed compounds.

The composition can be administered as a single once-a-day dose or as divided doses throughout a day. In some embodiments, the daily dose is administered twice daily in equally divided doses. In other embodiments, the daily dose is administered three times per day. In particular embodiments, the daily dose is administered three times per day in equally divided doses. In particular embodiments, the daily dose is administered four times per day in equally divided doses. The actual dosage can be determined by a practitioner of skill in the art according to, for example, the subjects age, body weight, body mass index, or other factors. In certain embodiments, administration of a composition in the invention may be repeated daily. In certain embodiments and the administrations may be separated by at least 1 day, 2 days or 3 days.

An effective amount of a composition described herein will provide therapeutic benefit without causing substantial toxicity. Toxicity of a composition can be determined by standard pharmaceutical procedures in cell cultures or experimental animals, for example, by determining the $LD_{50}$ (that is, the dose lethal to 50% of the population) or the $LD_{100}$ (that is, the dose lethal to 100% of the population).

The therapeutic index is the dose ratio between therapeutic effect and toxicity effect. Compounds that exhibit high therapeutic indices are preferred. The data obtained from these cell culture assays and animal studies can be used in formulating a dosage range that is not toxic for use in humans. The dosage of the compounds described herein lies preferably within a range of circulating concentrations that include the effective dose with little or no toxicity. The dosage may vary within this range depending upon the dosage form employed and the mute of administration utilized. The exact formulation, route of administration and dosage can be chosen by the individual physician in view of the patient's condition and the indication to be treated. (See, e.g., Fingl et al., 1996, In: The Pharmacological Basis of Therapeutics, $9^{th}$ ed., Chapter 2, p. 29, Elliot M. Ross).

The descriptions of exemplary doses are merely alternative descriptions that may be used optionally at the discretion of the physician and are not intended to conflict or supersede other descriptions of doses disclosed herein. The pharmacological action of preparations of the disclosed compounds is demonstrated by the disclosed biological examples.

Cochlear Implants for Administering Pharmaceutical Compositions Selected from Formulas (II)-(V)

The present disclosure contemplates administration of pharmaceutical compositions selected from formulas (II)-(V) using a suitable medical device implanted into the cochlea Cochlear implants can be used for actively programmed or passive administration of pharmaceutical compositions selected from formulas (II)-(V). Cochlear implants for delivering pharmaceutical compositions to the inner ear are well known in the art. See, for examples, P. Gibson, U.S. Pat. No. 7,571,012, entitled APPARATUS FOR DELIVERY OF PHARMACEUTICALS TO THE COCHLEA; A. Edge et al., U.S. Pat. No. 8,188,131, entitled COMPOUNDS THAT ENHANCE ATOH1 EXPRESSION; P. Gibson, U.S. Pat. No. 8,401,674, entitled APPARATUS FOR DELIVERY OF PHARMACEUTICALS TO THE COCHLEA; K. Debruyne et al., U.S. Pat. No. 8,515,560, entitled MEDICAL IMPLANT DRUG DELIVERY DEVICE, which are incorporated by reference in their entireties.

Kits

The present disclosure contemplates kits comprising compositions selected from formulas (II)-(V). Such kits may include compositions selected from formulas (II)-(V) configured in a ready-to-use dosage forms amenable for emergency administration on-the-field (for example, away from hospital settings, such as in combat situations) to subjects suffering from hearing loss and noise-induced disorders and conditions. Such kits may include any pharmaceutically acceptable dosage form of compounds selected from formulas (II)-(V) and optionally instructions for administration of a pharmaceutically acceptable dosage form of compounds selected from formulas (I)-(V).

EXAMPLES

Example 1

Materials

Antibodies: Mouse anti TuJ1 (Covance); Nuclear Yellow (Hoechst); Dulbecco's phosphate buffered saline without calcium or magnesium (DPBS; Sigma Aldrich, St Louis, Mo. #D8537); glucose (45%) (Sigma Aldrich #G8769); Dispase (Calbiochem, San Diego, Calif. #322120); DNAse (Sigma-Aldrich #D4513); DMEM/F12 (Sigma Aldrich #D6421); L-glutamine (Sigma-Aldrich #G6392); N2 mix (Invitrogen, Carlsbad, Calif. #17501048); Neurotrophic factor 3 (NT3) and Brain Derived Neurotrophic Factor (BDNF) were purchased from Promega (Madison, Wis.); Leukemia Inhibitory Factor, LIF (Sigma Aldrich); fetal bovine serum (Sigma Aldrich F2442), Polystyrene 384 well plates precoated with poly-D-lysine (Becton Dickinson Labware); Laminin (Sigma-Aldrich, L2020); mouse TuJ1 monoclonal antibody (Covance, Berkeley Calif.); Triton-X-100; Bone morphogenetic protein 4, BMP4 (R&D Systems, Minneapolis, Minn.); H1152, fasudil, hydroxyfasudil (all from EMD Chemicals, Gibbstown, N.J.); DMSO, Sigma; paraformaldehyde (EM Reagents); Alexafluor 594 labeled goat anti mouse IgG (Invitrogen); Nuclear Yellow (Hoechst, Invitrogen). HCA Vision computer software (CSIRO, Australia).

Example 2

In Vitro Screening Assay Procedures

Animal.

CD-1 mice (Charles River Laboratories, Wilmington Mass.), age newborn, were used for cultures that test neurite length; postnatal day 1-2 mice were used for cultures that test survival. Mice were anesthetized by cooling at −80° C. for 4 minutes and euthanized by aseptic decapitation.

Solutions.

Dissecting Buffer I: DPBS containing 1.4 mls of 45% glucose. Dispase solution: DPBS containing Dispase at 5 units/ml. Dissecting Buffer II: Dissecting Buffer I containing DNAse at a final concentration of 10μ/ml. Dissociation medium: DMEM/F12 containing 2 mM L-glutamine, N2 mix (1:100); 0.63 mls of 45% glucose for each 100 ml of DMEM/F12. Growth factor mix: Dissociation medium plus 20 ng/ml each NT3 and BDNF with or without LIF (100 ng/ml) or BMP4 (50 ng/ml), plus 20% fetal bovine serum, previously heat inactivated.

Culture Plates:

Polystyrene, multiwell plates (384 well) pretreated with poly-D-lysine were coated with laminin 24 hours before preparation of cultures. A cold stock solution of 101 g/ml of the protein was applied in a 50 μl volume to the odd numbered wells of a cold poly-D-lysine coated plate. The plate was refrigerated overnight and the next day was washed three times with DPBS. The third wash was left on the wells and the dishes were placed into the incubator at 34° C., 96% air/4% $CO_2$. At least two hours before dissection the DPBS was removed from the wells and 25 μl of growth factor mix was added to all of the odd numbered wells (194 wells). The plate was returned to the incubator until needed for plating the cells.

Procedure.

All supplies and instruments that were not sterile when purchased were autoclaved. Eight animals (16 cochleas) were used for each experiment. Cry-anesthetized newborn mice (for neurite length cultures) or postnatal day 1-2 (for survival cultures) were pinned out and wiped with 70% ice cold ethanol. The skin was removed, the skull and brain were bisected along the sagittal plane and each half of the skull+brain was removed to a separate 35 mm sterile suspension culture dish containing sterile Dissecting Buffer I at room temperature. Further dissection was continued under a microscope in a sterile environment, frequently transferring the partially dissected tissue to fresh, sterile Dissecting Buffer I. The encapsulated cochlea with its attached vestibular apparatus was removed from the skull. Extra tissue, particularly the vestibular ganglion and brain, was carefully dissected away. A piece of the capsule was cut away without cutting the underlying cochlea by inserting a point of a pair of Dumont #5 forceps into the round window of the capsule and alternately cutting the capsule and separating the cochlea from the inside surfaces. After the cochleas were thus dissected, the encapsulated cochleas were placed into a room temperature solution of Dispase at a concentration of 8 cochleas/0.75 mls and subsequently incubated at 34° C. for 40 min. Four cochleas each were transferred to 35 mm sterile suspension culture dishes containing Dissecting Buffer I (at room temperature) and maintained at room temperature for 40 minutes before further dissection in Dissecting Buffer II. The cochleas were placed into drops of Dissecting Buffer II in a 100 mm petri dish. The cochleas were carefully removed from the capsules with Dumont #5 forceps. The spiral ligament and stria vascularis were removed. Using the tip of a ½" insulin syringe, the epithelium, which came away in large sheets, was cut away and discarded. The remaining tissue contained the spiral ganglion, the spiral lamina, the modiolus and the limbus. The tissue was washed twice with Dissecting Buffer I—each in its own drop. They were then pushed together into one group and the buffer was removed. The tissue was collected in 5 mls of 34° C. dissociation medium in a 50 ml polypropylene centrifuge tube and was triturated by pulling the tissue and dissociation medium up and down 40 times with a 1 ml Pipetman pipette. The suspension was transferred to a 15 ml graduated polypropylene centrifuge tube and the volume was brought to 5.5 mls with additional warm dissociation medium. The suspension was transferred to a 50 ml reagent reservoir. Using a 12 channel pipetter, 25 µl of the suspension was aliquotted into each of the prepared odd numbered wells in the culture dish. The cultures were returned to the incubator. The final concentration of growth factors was 10 ng/ml for BDNF and NT3, 50 ng/ml for LIF, and 25 ng/ml for BMP4. All wells for neurite growth assays contained BDNF, NT3 and serum. For survival assays, 4 wells contained BDNF and NT3, 4 wells contained BDNF, NT3 and LIF, and the remaining wells contained serum with no neurotrophins. For survival assays, the tested compounds were added immediately after the cell suspension. For neurite growth assays, the tested compounds were added 22 hours later. After additions, the cultures were maintained for an additional 24 hours before fixation and staining.

Addition of Test Compounds:

For survival studies, test compounds were added immediately after the cell suspension. The 4 wells with BDNF+NT3 and the 4 wells with BDNF+NT3+LIF served as positive control to demonstrate the ability to survive 24 hours in culture. DMSO added to cultures that contained serum with no neurotrophins served as the negative control. For neurite length studies, test compounds were added 22 hours after plating. Negative controls were 4 wells of DMSO, 0.0825% and 4 wells of water 0.165%. Positive control was H1152, in water, at 16.5 uM.

Test compounds (10 mM) in DMSO were aliquotted to multiwell dishes and frozen by the High Throughput Laboratory at Northwestern University. These were allowed to thaw, then centrifuged in a PCR centrifuge for a few seconds. Additional test compounds (DMSO, water, or H1152) were placed in additional wells. To each well containing compound, 20 µl of dissociation medium was added using a multichannel pipette. The dish was sealed with an aluminum foil covering and centrifuged again for a few seconds. Using a multiwell pipetter, 4.5 µl of each solution was added to each of 4 replicate wells in the culture plate. Final concentrations: 8.25 µM test compounds; 0.0825% DMSO; 0.165% water, 16.5 µM H1152.

Fixation and Staining.

Cultures were fixed for 30 minutes at room temperature with 4% paraformaldehyde in 0.1M sodium phosphate buffer, pH 7.4. Cultures were washed 3×5 minutes with Tris Buffered Saline, pH 7.6 (TBS) using a 96 channel pipetter. Cultures were treated with 0.3% Triton X100 in TBS for 2 hours at room temperature. After washing 3 times with TBS, nonspecific staining was blocked with a solution of 5% bovine serum albumin (BSA)+10% normal goat serum (NGS) in TBS for 1 hour at room temperature. The monoclonal antibody TuJ1 was diluted in 5% BSA+10% NGS+0.3% Triton X 100 in TBS, added to wells, and maintained overnight at 4° C. After washing twice with TBS, Alexafluor 594 conjugated goat anti-mouse IgG was centrifuged and filtered to removed particulates. It was then diluted in 0.1% Triton in TBS, added to the wells and maintained for 4 hours at room temperature in the dark. The cultures were washed 3 times with TBS, then 0.001% Nuclear Yellow was added for 5 minutes at room temperature to label the nuclei. After washing twice with TBS, the cultures were preserved with a few drops of DAKO fluorescent mounting medium in each well.

Imaging Counting and Measuring.

Plates were automatically imaged using the ArrayScan VTi at 10×, 16 no-overlapping fields per well (about 80% of the surface area) using two filter sets targeting nuclei (Nuclear yellow) and the immunostained neurons (Alexafluor 594). An object was classified as a neuron if it had a nucleus and fell within the parameters set for size, shape and fluorescence intensity. The parameter setting excluded aggregated cells and background. Once optimized parameters were established, images were processed by the Cellomics software Neuronal Profiling Bioapplication to count neurons. Cellomics did not sufficiently detect fine neurites in the dish. For this, the software HCA vision was used. The longest neurite per neuron was identified and calculated in pixels. Cumulative percent histograms of neurite lengths were calculated and plotted with the software GraphPad. Histograms of each of the replicate wells were averaged. Graphs were visually inspected to determine initial "hits". Compounds that generated histograms that were similar to the positive control and any compounds that were possibly similar to the positive control were retested in new experiments. Compounds that continued to generate histogram similar to the positive control was retested at different concentrations. Similar compounds were also tested at different concentrations. For the statins, geranylgeraniol (10 µM) was added alone or with the statin to evaluate possible mechanisms. The most promising hits were advanced to in vive evaluation.

Example 3

Animal Model Screening Procedures

Drug efficiency was tested in guinea pigs, 200-500 g in bodyweight. The approach was as follows. Baseline cochlear function was determined with auditory brainstem responses. Sound levels to evoke a visual ABR response were determined for pure tones at selected frequencies between 2 and 32 kHz and for acoustic clicks. Delay times and amplitudes for wave I-V of the ABR were measured. A small ~180 μm catheter was surgically implanted into scala media of the cochlear basal turn. Through this catheter the drug dissolved in a carrier was delivered with an osmotic pump. After the pump implantation, the animals were allowed to recover from anesthesia. The animals were exposed to broadband noise (4-8 kHz or 8-16 kHz at 100-120 dB for 1-4 h). Noise exposure was always after baseline cochlear function was established 10 and 1 week before pump implantation to determine the ability of the drug to repair and reverse degeneration, and during recovery from implantation surgery to determine the ability of the drug for rescue, and protection. The drug was delivered for four weeks at a rate of 02511 using a microosmotic pump. After implantation, cochlear function was tested on a weekly basis using auditory brainstem responses (ABRs) or compound action potentials (CAPs, which are gross electrical responses from the cochlea) with the chronically implanted electrode. CAPs were performed at day 0 (pump implantation), ABRs and CAPs at day 1 (day of pump and electrical implant surgery), day 7, day 14, day 21, at day 28. (Day of CAP recording and animal euthanasia). At the conclusion of the 4 weeks of drug delivery, a final assessment of cochlear function was done and the cochleae were harvested for histology and hard x-ray scanning. Changes in sound levels required to evoke and ABR and the amplitude at maximum output levels of the speaker were compared among drug-treated noise-exposed and non-exposed animals. An ANOVA and Tukey honesty test were used to determine whether the ABR thresholds differed among the animals. Furthermore the delay time and amplitude for the five waves in the ABR were examined. If the threshold for stimulation obtained in noise exposed animals that were treated with the drug were lower and the maximum amplitudes are larger when compared to the values obtained from noise exposed but not treated animals, the drug was considered effective.

Anesthesia and Pump and Electrical Stimulator Implantation Surgery:

Animals received an initial intraperitoneal injection of Ketamine/Xylazine (40-80/5-10 mg/kg). For Ketamine/Xylazine a maintenance dose (20-33% of original dose of Ketamine/Xylazine) was given during the experiment if the animal showed signs of increasing arousal. In some cases, isoflurane was used for anesthesia. Anesthesia was induced by placing the animal (guinea pig) in an induction chamber ventilated with 5% isoflurane. After induction of the anesthesia, it was maintained by 0-3% isoflurane+0-50% nitrous oxide, typically at 0.5% isoflurane+50% nitrous oxide+49.5% oxygen. The cochlea was accessed by surgically opening the bulla. A c-shaped skin incision was made behind the left ear lobe and the cervicoauricular muscles were removed by blunt dissection. The left bulla was exposed and opened approximately 2×3 mm with a motorized drill. To measure compound action potentials (CAPs), a silver ball electrode was placed on the round window. To measure auditory brainstem responses, electrodes were placed behind the bulla, at the vortex and remotely under the skin. The basal turn of the cochlea was identified and a cochleostomy was created, approximately 0.5 mm from the bony rim of the round window. After the cochleostomy was made in the basal cochlear turn, the connecting tubing from the osmotic pump and/or the electrode for electrical stimulation and/or CAP recording was inserted through the opening of the cochlear wall. The drug container of the pump was secured below the skin between the shoulder blades. To access the placement site for the drug container, a tunnel was bluntly dissected from the incision site for the bullotomy towards the shoulder blades. For the electrical stimulator, the wires were secured in the bulla with dental acrylic. A small incision (less than 5 mm) was made along a line connecting both ear lobes. A connector was secured with two short screws on the scull. Furthermore, the placement of the connector was accomplished with dental acrylic. After the pump was in place, the tubing was cemented in place with dental acrylic, the bulla was closed with dental acrylic, and the skin was closed in two layers with 4.0-5.0 absorbable suture material. The skin was closed with non-absorbable 4.0-5.0 suture material using an interrupted suture technique. Sutures were removed after 2 weeks during a hearing assessment.

Anesthesia and Non-Survival Surgery:

Urethane, was used to induce anesthesia during non-survival guinea pig surgeries. Urethane (4.5 ml/kg, 20% solution in phosphate buffered saline) was introduced via intraperitoneal injection. Induction of anesthesia was achieved by one urethane injection, and anesthesia maintenance was achieved with ketamine/xylazine or with isoflurane (0-5%)+nitrous oxide (0-50%). Animals also received an initial intraperitoneal injection of Ketamine/Xylazine (40-80/5-10 mg/kg). For Ketamine/Xylazine a maintenance dose (20-33% of original dose of Ketamine/Xylazine) was given during the experiment if the animal showed signs of increasing arousal. Likewise, isoflurane was used for anesthesia. Anesthesia was induced by placing the animal (guinea pig) in an induction chamber ventilated with 5% isoflurane. After induction of the anesthesia, it was maintained by 0-3% isoflurane+0-50% nitrous oxide, typically at 0.5% isoflurane+50% nitrous oxide+49.5% oxygen. Core body temperature was maintained at 38° C. with a thermostatically controlled heating pad. Heart rate, respiratory rate and $O_2$ saturation was monitored and recorded every 15 minutes. Once a sufficient anesthetic plane had been reached, the cochlea was accessed by surgically opening the bulla. A c-shaped skin incision was made behind the left ear lobe and the cervicoauricular muscles were removed by blunt dissection. The cartilaginous outer ear canal was exposed and cut to insert an ear bar into the ear canal. The bulla was exposed and opened approximately 2×3 mm with a motorized drill. To measure compound action potentials (CAPs), a silver ball electrode was placed on the round window. To measure auditory brainstem responses, electrodes were placed behind the bulla, at the vortex and remotely under the skin.

Compound Action Potentials (CAPs):

To measure compound action potentials (CAPs), a silver ball electrode was placed on the round window. Acoustically evoked compound action potentials were measured using a modified tracking procedure (Taylor and Creelman, 1967; Gummer et al., 1987). CAPs were determined between 50 kHz-2 kHz. The acoustic stimuli were 12 ms tonebursts, (including 1 ms rise time and 1 ms fall time). CAP threshold was defined as 20±2 μV (N1/P1 amplitude). Thirty-two waveforms, presented in opposite phase, were averaged for a single measurement. Acoustic clicks are generated as 50 μs pulses.

Auditory Brainstem Responses (ABRs):

Three needle electrodes were placed under the skin to obtain ABRs by subtracting ipsilateral mastoid from vertex potentials measured relative to a ground electrode placed in the neck. Acoustic stimuli were generated by a voltage command presented at a rate of 4 Hz to a Beyer DT 770-Pro headphone, which had been previously calibrated with a Bruel and Kaer ⅛-in microphone. The speculum of the speaker was placed directly in front of the ear canal (quasi free field). The frequency for the tonebursts started at 32 kHz and decreased in several steps over 5 octaves. Acoustic clicks were speaker responses to 50 µs long voltage pulses. Sound levels, began at the loudest speaker output and decrease in 5 dB steps. The loudest speaker output varied from 71 dB to 101 dB, depending on the frequency and was 80 dB SPL peak for the click. The ABR electrodes were connected to a differential amplifier (ISO-80, WPI) with an high-input impedance ($>10^{12}\Omega$), set at 10,000× amplification. Further amplification (ten times) and filtering (0.3 to 3 kHz) of the signal was obtained through a digital filter (IP90, Frequency Devices). The sampling rate was 200 kHz and 100-1024 trials were averaged. Threshold was defined as an ABR that was visible above the noise floor of the recordings, which was typically ~0.5 µV.

Histology:

Following fixation, the cochleae and surrounding bone was decalcified using either 10% EDTA bath (pH 7.0) or by incubation at 38° C. for 24-28 hours in 0.1M HCl and 1M Formic acid. Decalcified cochleae was dehydrated in graded ethanol baths from 50-100%, in steps of 10%. Baths were repeated three times for 30 min for each ethanol concentration. For Paraplast embedding, clearing was performed with at least three changes of xylene until the tissue is fully translucent. Infiltration of the embedding medium was performed with a total of four changes of molten paraffin wax (Paraplast Xtra, Leica Biosystems), each for 15 min under vacuum at 56° C. Cochleae were oriented within a tissue mold and embedded in the paraffin wax. Tissue blocks were sectioned at 10 µm with a rotary microtome. Tissue sections were collected on Superfrost Plus (VWR) glass slides and adhered by overnight incubation at 58° C. For staining, sections were de-waxed and hydrated through baths of xylene (3 changes, 2 min), 100% ethanol (2 changes, 2 min), 95% ethanol (3 changes, 2 min) and water. Sections were stained with hematoxylin or toluidine blue and the reverse of de-waxing regimen were performed and coverslips applied with Permount (Fisher Scientific). Digital photomicrographs were taken using standard transmitted light microscopy. Using the images of the cochlear histological sections, the presence of the basilar membrane, tectorial membrane, outer hair cells, inner hair cells, and supporting cells will be visually evaluated. Additionally, tissue growth in the cochlea was quantified. Spiral ganglion neurons were counted and the density of the neurons in Rosenthal's canal, were determined (Whitlon et al. 2006 Richter et al., 2008). The first section at the basal cochlear end that contained spiral ganglion neurons was displayed in Adobe Photoshop. An additional layer was inserted on the image and a circle of the approximate size of the neuronal cell nuclei was marked on the layer for each cell counted. Characteristic landmarks were also added to align the image on the next section. After the cells in section 1 were counted, the corresponding image of section 2 was opened. The inserted layer from section 1 was then copied onto section 2. The images were aligned so that the landmarks superimpose. This clearly identified the cells from section 1 that were already counted. Another layer was inserted on the image, and the cells in section 2 that were not counted in section 1 were then counted and marked on the inserted layer. This then identified the already counted cells in section 2 and allowed them to be omitted in the counts of section 3, and so on. In this way, every neuron in the cochlea was counted without systematic errors due to over- or under-counting. To simplify the counting, we did not distinguish between type I and type II spiral ganglion neurons. The cross sectional area of Rosenthal's canal was measured on digital images using ImageJ (Wayne Rasband, NIH). Area measurements of Rosenthal's canal were obtained by tracing the shortest line encircling the spiral ganglion neurons. The total number of pixels within a circumscribed area was calculated and converted into square millimeters. Neuron density per square area was calculated by dividing the neuron counts by the corresponding area. The corresponding volume density was calculated by dividing the number of neurons counted by the volume (sum of the square areas times the slice thickness).

X-Ray Imaging:

Cochleae from the guinea pigs were be harvested. Next, the specimens were stained with osmium tetroxide (1% for 60 minutes). Osmium tetroxide is a common stain for electron microscopy because it reacts with unsaturated fatty acids to increase X-ray absorption (White et al., 1976). Thus, osmium staining optimized visualization of lipid-rich membranes and myelinated structures such as spiral ganglion neurons and nerve fibers in the cochlea. Micro-computed tomography (microCT) was carried out at the 2-BM beamline at the Advanced Photon Source (APS) at Argonne National Laboratory (Argonne, Ill., USA) using either a 5× or 10× objective lens. The field of view using the 5× lens was 3×4 mm, requiring two full scans of 20 minutes each to capture the entire specimen. Similarly, two scans were used to visualize the cochlea using the 10× lens. A series of phase contrast X-ray projections were taken over a range of 180 degrees at increments of 0.125 degrees. Reconstructions were on a 2K×2K grid and resulted in 1.45 µm isotropic voxels with the 5× objective lens and in 0.78 µm isotropic voxels with the 10× lens. While the sites for examination are limited in classical histology, stacks of reconstructions obtained through microCT can be used to orient the specimen freely, reorientation is easy and possible.

Automated Counting of Neurons from X-Ray Images:

We subjected the X-ray images to an automated counting program to decrease analysis time as well as human error. The program measured the gray value of each pixel to determine the location of the neurons in each X-ray image. Since the gray values of neurons were substantially higher than the surrounding structures due to the osmium stain, peaks in the plot profile correspond to neurons in the X-ray image. To count the neurons, the software loaded a user-cropped sequence of X-ray slices and each slice was examined pixel-by-pixel. A pixel was recognized as a neuron if the following criteria were fulfilled: the intensity of the gray value was above a user selected threshold value for the selected pixel as well as for the 2 neighboring pixels in both the positive and negative x direction. Additionally, the third neighbor in the positive and negative x direction must have been below the threshold. When these criteria were met, the same procedure was repeated along the y-axis, followed by the z-axis. If all these criteria were satisfied, the pixel indicated the center of a high-intensity sphere with a diameter of 5 pixels in the stack of slices, which corresponded to a neuron with a diameter of ~7.25 µm in the spiral ganglion. Once a neuron had been identified, it was added to a running counter, and a dead space the size of a neuron was created in the result matrix to ensure double counting did not occur. The program also overlayed an image of the newly counted neurons with the original image, allowing the investigator to verify that only neurons are counted and that no double counting occurred.

REFERENCES

All patents, patent applications, patent application publications and other publications that are cited herein are hereby incorporated by reference as if set forth in their entirety.

It should be understood that the methods, procedures, operations, composition, and systems illustrated in the figures may be modified without departing from the spirit of the present disclosure. For example, these methods, procedures, operations, devices and systems may comprise more or fewer steps or components than appear herein, and these steps or components may be combined with one another, in part or in whole.

Furthermore, the present disclosure is not to be limited in terms of the particular embodiments described in this application, which are intended as illustrations of various embodiments. Many modifications and variations can be made without departing from its scope and spirit. Functionally equivalent methods and apparatuses within the scope of the disclosure, in addition to those enumerated herein, will be apparent to those skilled in the art from the foregoing descriptions.

We claim:

1. A method of stimulating neurite growth from spiral ganglion neurons in the inner ear, comprising contacting a neurite with a statin, or a pharmaceutically acceptable salt thereof, wherein the statin comprises a compound selected from a group consisting of compounds having formulas (II)-(VII):

(II)
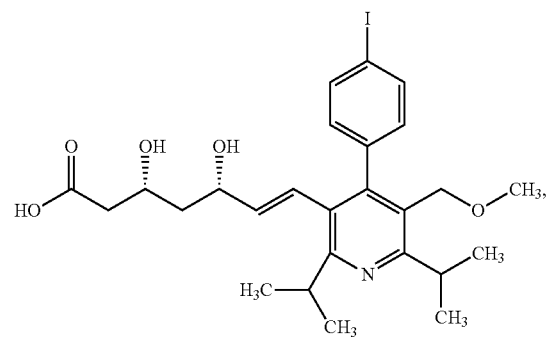

(III)
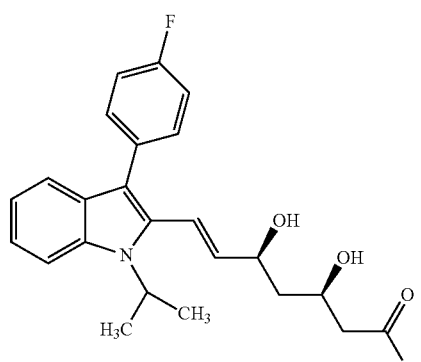

(IV)
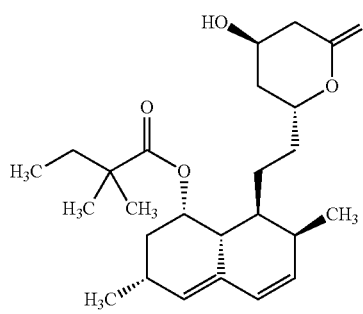

(V)
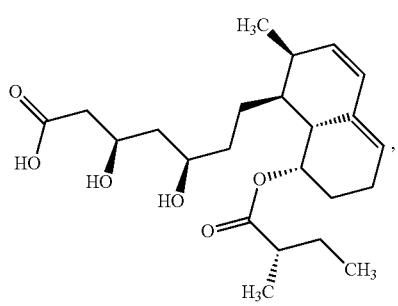

(VI)
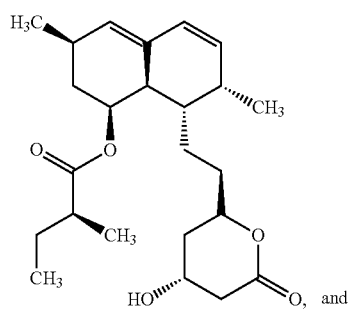

and (VII)
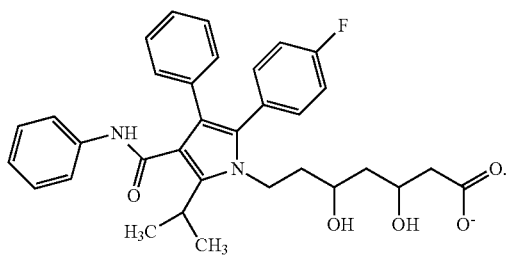

2. The method of claim 1, wherein the statin comprises a compound having the structure of formula (III):

(III)
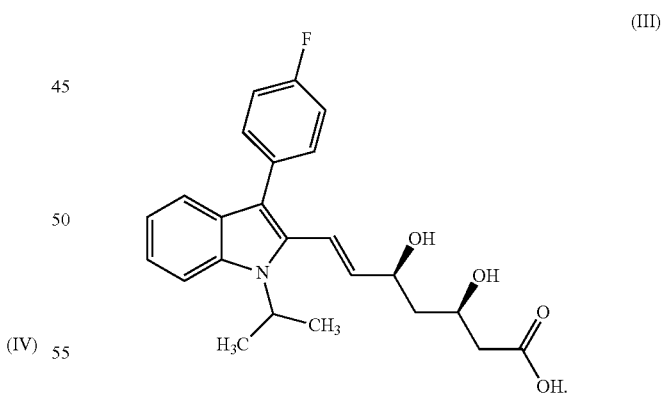

3. The method of claim 1, wherein the contacting step comprises incubating the neurite with a culture medium comprising the statin.

4. A method of preventing or treating hearing loss in a subject, comprising administering to the subject a statin or a pharmaceutically acceptable salt thereof, wherein the administering step comprises contacting a cochlea of the subject with a pharmaceutical composition of a statin or a pharmaceutically acceptable salt thereof, further wherein the statin comprises a compound selected from a group consisting of compounds having formulas (II)-(VII):
(II)
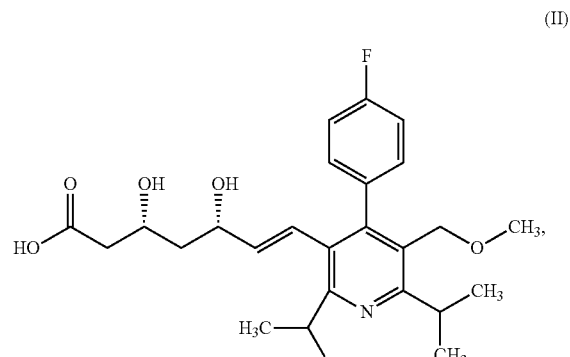
(III)
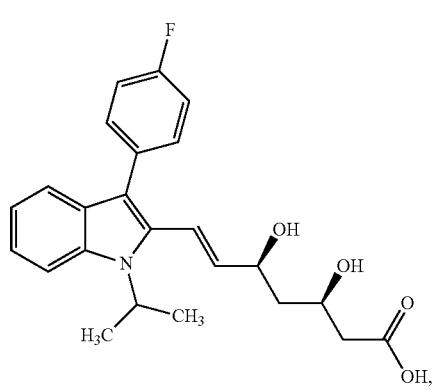
(IV)
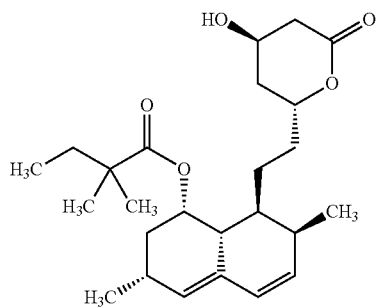
(V)
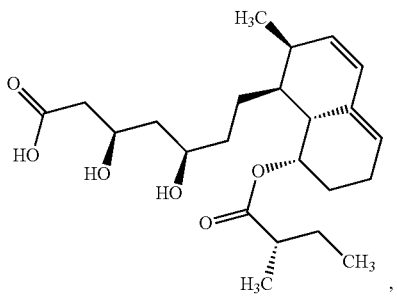
(VI)
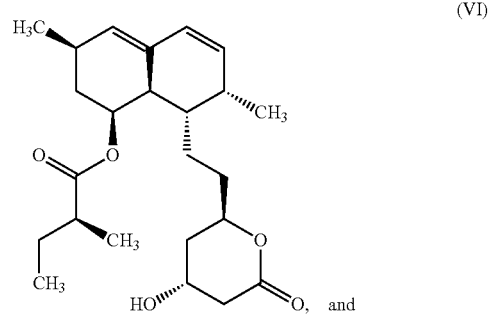
(VII)
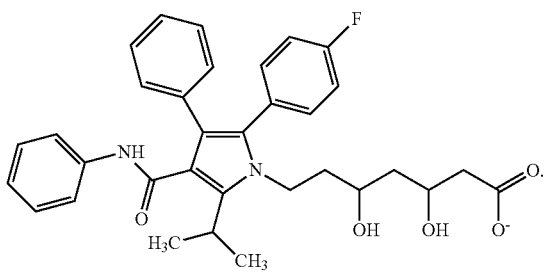
5. The method of claim 4, wherein the subject is a human.
* * * * *